US009153142B2

(12) United States Patent
Bagchi et al.

(10) Patent No.: US 9,153,142 B2
(45) Date of Patent: Oct. 6, 2015

(54) USER INTERFACE FOR AN EVIDENCE-BASED, HYPOTHESIS-GENERATING DECISION SUPPORT SYSTEM

(75) Inventors: Sugato Bagchi, White Plains, NY (US); Michael A. Barborak, New York, NY (US); Steven D. Daniels, Merrick, NY (US); David A. Ferrucci, Yorktown Heights, NY (US); Anthony T. Levas, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 88 days.

(21) Appl. No.: 13/448,607

(22) Filed: Apr. 17, 2012

(65) Prior Publication Data
US 2012/0301864 A1      Nov. 29, 2012

Related U.S. Application Data

(60) Provisional application No. 61/490,427, filed on May 26, 2011.

(51) Int. Cl.
*G09B 7/00*     (2006.01)
*A61B 5/00*     (2006.01)
(Continued)

(52) U.S. Cl.
CPC ... *G09B 7/02* (2013.01); *A61B 5/00* (2013.01); *G06N 5/02* (2013.01); *G09B 7/00* (2013.01)

(58) Field of Classification Search
CPC ...... G09B 7/02; G09B 7/00; G06F 17/30672; G06F 17/30864; G06F 19/3431; G06F 19/3443; G06F 17/30613; G06F 17/30716; G06F 17/30728; G06N 3/004; G06N 5/043; G06N 99/005; G06N 5/02; G06Q 10/10; G06Q 10/00; G06Q 50/22; G06Q 50/24; G06Q 40/00; A61B 5/00
USPC .................. 707/3, 5, 6, 7, 713, 715; 705/2, 3; 600/300; 434/322, 362; 706/14, 21, 50
See application file for complete search history.

(56) References Cited

U.S. PATENT DOCUMENTS 6,292,796 B1 *   9/2001   Drucker et al. ........................ 1/1
6,438,533 B1     8/2002   Spackman et al.
(Continued)

FOREIGN PATENT DOCUMENTS

WO        0150330 A1     7/2001

OTHER PUBLICATIONS

Cao et al., Askhermes: an online answering system for complex clinical questions, Jan. 2011.*
(Continued)

*Primary Examiner* — Sam Yao
*Assistant Examiner* — Eddy Saint-Vil
(74) *Attorney, Agent, or Firm* — Gibb & Riley, LLC

(57) ABSTRACT

Systems and methods display at least one subject, and display a location for at least one user to enter at least one problem related to the subject. The problem comprises unknown items to which the user would like more information. In response to the problem, such systems and methods automatically generate evidence topics related to the problem, and automatically generate questions related to the problem and the evidence topics. Further, such systems and methods can receive additional questions from the user. In response to the questions, such systems and methods automatically generate answers to the questions by referring to sources, automatically calculate confidence measures of each of the answers, and then display the questions, the answers, and the confidence measures. When the user identifies one of the answers as a selected answer, such systems and methods display details of the sources and the factors used to generate the selected answer.

24 Claims, 20 Drawing Sheets

(51) Int. Cl.
*G09B 7/02* (2006.01)
*G06N 5/02* (2006.01)
*G06N 5/00* (2006.01)

(56) References Cited

U.S. PATENT DOCUMENTS

| | | | |
|---|---|---|---|
| 6,527,713 B2* | 3/2003 | Iliff | 600/300 |
| 7,149,756 B1 | 12/2006 | Schmitt et al. | |
| 7,225,183 B2* | 5/2007 | Gardner | 1/1 |
| 7,344,496 B2 | 3/2008 | Iliff | |
| 8,032,398 B1* | 10/2011 | Kelly et al. | 705/3 |
| 2003/0105638 A1 | 6/2003 | Taira | |
| 2004/0122702 A1* | 6/2004 | Sabol et al. | 705/2 |
| 2005/0010444 A1 | 1/2005 | Iliff | |
| 2006/0015498 A1* | 1/2006 | Sarmiento et al. | 707/6 |
| 2007/0067293 A1* | 3/2007 | Yu | 707/7 |
| 2008/0052122 A1 | 2/2008 | Iliff | |
| 2008/0059453 A1* | 3/2008 | Laderman | 707/5 |
| 2008/0082357 A1 | 4/2008 | Schmitt et al. | |
| 2008/0201280 A1 | 8/2008 | Martin et al. | |
| 2008/0301120 A1* | 12/2008 | Zhu et al. | 707/5 |
| 2009/0030856 A1* | 1/2009 | Arena et al. | 706/11 |
| 2009/0162824 A1* | 6/2009 | Heck | 434/322 |
| 2009/0292557 A1* | 11/2009 | Sirohey et al. | 705/3 |
| 2010/0076780 A1* | 3/2010 | Mahesh et al. | 705/2 |
| 2010/0131438 A1 | 5/2010 | Pandya et al. | |
| 2010/0153332 A1 | 6/2010 | Rollins et al. | |
| 2010/0235378 A1 | 9/2010 | Armstrong et al. | |
| 2010/0280847 A1 | 11/2010 | Schaffer | |
| 2010/0318549 A1 | 12/2010 | Mayr et al. | |
| 2011/0004588 A1 | 1/2011 | Leitersdorf et al. | |
| 2011/0055190 A1 | 3/2011 | Alexander | |
| 2011/0055240 A1 | 3/2011 | Li et al. | |
| 2012/0005148 A1* | 1/2012 | Horvitz et al. | 706/50 |
| 2012/0041950 A1* | 2/2012 | Koll et al. | 707/728 |
| 2012/0131016 A1 | 5/2012 | Brown et al. | |
| 2013/0041921 A1* | 2/2013 | Cooper et al. | 707/780 |

OTHER PUBLICATIONS

Mendonça et al., Answering Information Needs in Workflow, 2005.*
Yu et al., Automatically Extracting Information Needs from Ad Hoc Clinical Questions, 2008, 96-100.*
Fushman et al., Answering Clinical Questions with Knowledge-Based and Statistical Techniiques, 2007.*
Kasneci et al., NAGA: Searching and Ranking Knowledge, Mar. 2007.*
Barnett, G.O., Cimino, J.J., Hupp, J.A., Hoffer, E.P. DXplain: An evolving diagnostic decision-support system. JAMA 258, 1 (1987), 67-74.
Berner, E.S. Diagnostic Decision Support Systems: Why aren't they used more and what can we do about it? AMIA Annu. Symp. Proc. (2006), 1167-1168.
Sim, I., Gorman, P., Greenes, R.A., Haynes, R.B., Kaplan, B., Lehmann, H. and Tang, P.C. Clinical decision support systems for the practice of evidence-based medicine. J. Am. Med. Inform. Assoc. 8, 6 (2001), 527-534.
Cannon, D.S. and Allen, S.N. A comparison of the effects of computer and manual reminders on compliance with a mental health clinical practice guideline. Journal of the American Medical Informatics Association 7, 2 (2000), 196-203.
Warner, H.R., Haug, P., Bouhaddou, O., Lincoln, M., Warner, H., Sorenson, D., Williamson, J.W. and Fan, C. Iliad as an expert consultant to teach differential diagnosis. In Proc. Annu. Symp. Comput. Appl. Med. Care. (1988), 371-376.
Friedman, C.P., Elstein, A.S., Wolf, F.M., Murphy, G.C., Franz, T.M., Heckerling, P.S., Fine, P.L., Miller, T.M. and Abraham, V. Enhancement of clinicians' diagnostic reasoning by computer-based consultation: A multisite study of 2 systems. JAMA 282, 19 (1999), 1851-1856.
Myers, J.D. The background of Internist-I and QMR. In Proceedings of ACM Conference on History of Medical Informatics (1987), 195-197.
Ramnarayan, P., Tomlinson, A., Rao, A., Coren, M., Winrow, A. and Britto, J. Isabel: A web-based differential diagnostic aid for paediatrics: Results from an initial performance evaluation. Archives of Disease in Childhood 88, 5 (2003), 408-413.
Ramnarayan, P., Roberts, G.C., Coren, M., Nanduri, V., Tomlinson, A., Taylor, P.M., Wyatt, J.C. and Britto, J.F. Assessment of the potential impact of a reminder system on the reduction of diagnostic errors: A quasi-experimental study. BMC Med. Inform. Decis. Mak. 6, 22 (2006).
Selker, H.P., Beshansky, J.R., Griffith, J.L., Aufderheide, T.P., Bailin, D.S., Bernard, S.A., Crespo, S.G., Feldman, J.A., Fish, S.S., Gibler, W.B., Kiez, D.A., McNutt, R.A., Moulton, A.W., Ornato, J.P., Podrid, P.J., Pope, J.H., Salem, D.N., Sayre, M.R. and Woolard, R.H. Use of the acute cardiac ischemia time-insensitive predictive instrument (ACI-TIPI) to assist with triage of patients with chest pain or other symptoms suggestive of acute cardiac ischemia: A multicenter, controlled clinical trial. Annals of Internal Medicine 129, 11 (1998), 845-855.
Shortliffe, T. Medical thinking: What should we do? In Proceedings of Medical Thinking: What Do We Know? A Review Meeting (2006). http://www.openclinical.org/medicalThinking2006Summary2.html.
U.S. Appl. No. 13/077,464, Office Action Communication dated Nov. 14, 2013, 16 pages.
Denmer-Fushman et al., "Answering Clinical Questions with Knowledge-Based and Statistical Techniques", Association for Computational Linguistics, vol. 33, No. 1, 2007, p. 63-103.
Kathleen Ann McKibbon, "The Effect of Risk Attitude and Uncertainty Comfort on Primary Care Physicians' Use of Electronic Information Resources", University of Pittsburgh Center for Biomedical Informatics Faculty of Medicine, Dissertation, 2005, p. 100-180.
O'Sullivan et al., "Automatic indexing and retrieval of encounter-specific evidence for point-of-care support", Journal of Biomedical Information 43, 2010, p. 623-631.
PCT International Search Report, International Application No. PCT/US2012/027942, dated Aug. 21, 2012, pp. 1-10.
U.S. Appl. No. 13/077,464, Office Action Communication dated Mar. 7, 2014, 21 pages.
U.S. Appl. No. 13/077,464, Advisory Action dated May 29, 2014, 4 pages.
U.S. Appl. No. 13/077,480, Office Action Communication dated Jan. 17, 2013, 11 pages.
U.S. Appl. No. 13/077,480, Office Action Communication dated Jun. 10, 2013, 13 pages.
U.S. Appl. No. 13/077,480, Advisory Action dated Sep. 11, 2013, 3 pages.
International Application No. PCT/US2012/027936, PCT International Preliminary Report on Patentability, Mar. 7, 2012, pp. 1-6.
U.S. Appl. No. 13/077,480, Office Action Communication dated Apr. 9, 2014, 14 pages.
International Application No. PCT/US2012/027936, PCT International Search Report and Written Opinion, Mar. 7, 2012, pp. 1-9.
U.S. Appl. No. 13/077,480, Office Action Communication dated Sep. 3, 2014, 12 pages.
U.S. Appl. No. 13/077,464, Office Action Communication dated Sep. 22, 2014, 16 pages.
U.S. Appl. No. 13/077,464, Notice of Allowance dated Nov. 24, 2014, 5 pages.
David Ferrucci et al., "Building Watson: An Overview of the Deep QA Project", Copyright © 2010, Association for the Advancement of Artificial Intelligence. pp. 1-21, Fall, 2010.
Mark Graber, "Diagnostic Error in Internal Medicine", Arch Intern Med/vol. 165, Jul. 11, 2005 www.archinternmed.com., pp. 1-7.
Robert Trowbridge, MD, Chapter 53. Clinical Decision Support Systems, http://www.ahrq.gov/clinic/ptsafety/chap53.htm, Apr. 10, 2012., pp. 589-194.
David Ferrucci et al., IBM Research Report, "Towards the Open Advancement of Question Answering Systems", RC24789 Computer Science, Apr. 22, 2009, pp. 1-29.

(56) References Cited

OTHER PUBLICATIONS

David Ferrucci et al., IBM Research Report, "Watson: Beyond Jeopardy", RC25270 Computer Science, Jun. 2, 2011, pp. 1-11.
Unified Medical Language System® (UMLS®), UMLS MetaMap: http://www.nlm.nih.Gov/research/umls/implementation_resources/metamap.html, Apr. 12, 2012, pp. 1-2.
http://www.isabelhealthcare.com/home/, Apr. 16, 2012, p. 1.
www.autonomyhealth.com, Apr. 16, 2012, p. 1.
U.S. Appl. No. 13/077,480, Office Action Communication dated Dec. 10, 2014, 15 pages.
U.S. Appl. No. 13/077,480, Office Action Communication dated Apr. 17, 2015, 15 pages.
10-2013-7025364, Office Action dated Feb. 17, 2015, 8 pages.

* cited by examiner

Expanded Factors

Smith, Joanne     Profile Card     Dashboard

Factors

*Symptoms*

| | |
|---|---|
| The patient complains of red eye with pain and inflammation, particularly acute in the morning and nighttime. The condition began 2 weeks ago shortly after returning from a trip to Maine. | Source: Visit note<br>Date: 3/20/2011 |
| The patient also noted occasional blurred vision, floating spots and sensitivity to light. | Source: Visit note<br>Date: 3/20/2011 |

*Family History*

| | |
|---|---|
| Arthritis | Source: Patient information<br>Date: 6/10/2008 |

*Allergies*

| | |
|---|---|
| Penicillin | Source: Patient information<br>Date: 6/10/2008 |

*Demographics*

| | |
|---|---|
| 34 years old | Source: Patient information<br>Date: 6/10/2008 |
| Female | |

Scratchpad

FIG. 9

Evidence Source Detail 280

Textbook ★★★ ☆

Source: Uveitis and Immunological Disorders, Uwe Pleyer, Stephen Foster
Created: 2006

Uveitis is swelling and irritation of the uvea, the middle layer of the eye. The uvea provides most of the blood supply to the retina.

Causes, incidences, and risk factors

Uveitis can be caused by autoimmune disorders such as rheumatoid arthritis or ankylosing spondylitis, infection, or exposure to toxins. However, in many cases the cause is unknown.

The most common form of uveitis is anterior uveitis, which involves inflammation in the front part of the eye. It is often called iritis because it usually only affects the iris, the colored part of the eye. The inflammation may be associated with autoimmune diseases, but most cases occur in healthy people. The disorder may affect only one eye. It is common in young and middle-aged people.

Posterior uveitis affects the back part of the uvea, and involves primarily the choroid, a layer of blood vessels and connective tissue in the middle part of the eye. This type of uveitis is called choroiditis. If the retina is also involved, it is called chorioretinitis. You may develop this condition if you have had a body-wide (systemic) infection or if you have an autoimmune disease.

Another form of uveitis is pars planitis. This inflammation affects the narrowed area (pars plana) between the colored part of the eye (iris) and the choroid. Pars planitis usually occurs in young men and is generally not associated with any other disease. However, some evidence suggests it may be linked to Crohn's disease and possibly multiple sclerosis.

Uveitis can be associated with any of the following:

- AIDS
- Ankylosing spondylitis
- Behcet syndrome
- CMV retinitis
- Herpes zoster infection
- Histoplasmosis
- Injury
- Kawasaki disease
- Psoriasis
- Reactive arthritis
- Rheumatoid arthritis
- Sarcoidosis
- Syphilis
- Toxoplasmosis
- Tuberculosis
- Ulcerative colitis

USER INTERFACE FOR AN EVIDENCE-BASED, HYPOTHESIS-GENERATING DECISION SUPPORT SYSTEM

CROSS-REFERENCE TO RELATED APPLICATIONS

This application claims priority to the Provisional Application U.S. Patent Application No. 61/490,427 filed May 26, 2011, the complete disclosure of which, in its entirety, is herein incorporated by reference.

BACKGROUND

1. Field of the Invention

The present disclosure relates to a DeepQA-based technology, where users are presented a new question and answer tool for investigating problems.

2. Description of Related Art

In 2007, IBM® Research took on the grand challenge of building a computer system that can perform well enough on open-domain question answering to compete with champions at the game of Jeopardy!® In 2011, the open-domain question answering system dubbed Watson® beat the two highest ranked players in a two-game Jeopardy! match. But, to what degree can the question answering (QA) technology underlying Watson, a deep question answering system called DeepQA®, which was tuned for answering Jeopardy! questions, succeed in a dramatically different and extremely specialized domain such as medicine? This disclosure describes the steps used to adapt and improve performance in this as well as other domains. In addition, whereas Jeopardy! allows only "question in, single answer out" with no explanation, the disclosure elaborates upon a vision for an evidence-based clinical decision support system, based on the DeepQA technology, that affords exploration of a broad range of hypotheses and their associated evidence, as well as uncovers missing information that can be used in mixed-initiative dialog.

Jeopardy! is a quiz show that pits three contestants against each other testing their ability to understand and answer rich natural language questions very quickly. These questions often contain complex language, ambiguities, puns, and other opaque references. For any given question, the contestants compete for the first chance to answer via a handheld buzzer.

To be successful at Jeopardy!, players must retain enormous amounts of information, must have strong language skills, must be able to understand precisely what is being asked, and must accurately determine the likelihood they know the right answer. Confidence in the answer is critical, because the first player to buzz in gets the opportunity to answer the question; however, if the player answers incorrectly, the player loses the dollar value associated with the clue. The challenges in the Jeopardy! task are: 1) Questions come from a broad domain: Jeopardy! Asks questions about hundreds of thousands of things, using rich and varied natural language expressions. 2) Players must answer questions with high precision and with accurate confidence: On average, champion players must be able to correctly answer more than 85% of the questions they buzz in for and they must be confident enough to buzz in for at least 70% percent of them. 3) Answering must be very fast: Winning players must quickly determine an accurate confidence in a correct answer and buzz in quickly enough to beat their competitors consistently to the buzz.

Over a four year period, the team at IBM developed the Watson system that competed on Jeopardy! and the underlying DeepQA question answering technology (Ferrucci, D., Brown, E., Chu-Carroll, J., Fan, J., Gondek, D., Kalyanpur, A. A., Lally, A., Murdock, J. W., Nyberg, E., Prager, J., Schlaefer, N., Welty, C. *Building Watson: An Overview of the DeepQA Project*. AI Magazine, Fall 2010). Watson played many games of Jeopardy! against celebrated Jeopardy! champions and, in games televised in February 2011, won against the greatest players of all time, Ken Jennings and Brad Rutter. But, DeepQA has application well beyond Jeopardy! Contrary to some popular misconceptions, DeepQA does not map the question to a database of questions and simply look up the answer. DeepQA is a software architecture for analyzing natural language content in both questions and knowledge sources. DeepQA discovers and evaluates potential answers and gathers and scores evidence for those answers in both unstructured sources, such as natural language documents, and structured sources, such as relational databases and knowledge bases.

SUMMARY

An exemplary method herein displays, on a user interface, at least one subject (or allows the user to enter or select a subject) and displays a location for at least one user to enter at least one problem related to the subject. The problem comprises unknown items upon which the user desires to obtain additional information, such as a question or statement, for example. The method automatically generates questions related to the problem and the evidence topics using the computerized device. The method can also receive additional questions from the user through the user interface.

In response to the questions, the method automatically generates answers to the questions by referring to sources within the computerized storage medium using the computerized device. The method automatically calculates confidence measures of each of the answers using the computerized device. The method then displays the questions, the answers, and the confidence measures on the user interface. The method can also display how the sources contributed to the confidence measures of the answers on the user interface. When the user identifies one of the answers as a selected answer through the user interface, the method displays details of the sources and the factors used to generate the selected answer on the user interface.

Another exemplary method herein displays, on a user interface, at least one subject (or allows the user to enter or select a subject) and displays a location for at least one user to enter at least one problem related to the subject. The problem comprises unknown items upon which the user desires to obtain additional information, such as a question or statement, for example. In response to the problem, the method automatically generates evidence topics related to the problem using a computerized device operatively connected to the user interface, the evidence topics being categorized into dimensions of evidence.

Further, the method displays the evidence topics categorized into the dimensions of evidence on the user interface. The method can receive factors in response to the evidence topics from the user through the user interface and the method automatically retrieves additional factors from at least one computerized storage medium operatively connected to the computerized device. The method automatically generates questions related to the problem and the evidence topics using the computerized device. The method can also receive additional questions from the user through the user interface. The method can further receive an indication of which of the factors should be ignored and which of the factors should be considered from the user through the user interface.

In response to the questions, the method automatically generates answers to the questions by referring to the factors that should be considered and to sources within the computerized storage medium using the computerized device. The method automatically calculates confidence measures of each of the answers using the computerized device. The method then displays the questions, the answers, and the confidence measures on the user interface. The method can also display how the sources contributed to the confidence measures of the answers on the user interface. When the user identifies one of the answers as a selected answer through the user interface, the method displays details of the sources and the factors used to generate the selected answer on the user interface.

An additional exemplary method herein displays, on a user interface, at least one subject (or allows the user to enter or select a subject) and displays a location for at least one user to enter at least one problem related to the subject. The problem comprises unknown items upon which the user desires to obtain additional information, such as a question or statement, for example. In response to the problem, the method automatically generates evidence topics related to the problem using a computerized device operatively connected to the user interface, the evidence topics being categorized into dimensions of evidence.

Further, the method displays the evidence topics categorized into the dimensions of evidence on the user interface. The method can receive factors in response to the evidence topics from the user through the user interface and the method automatically retrieves additional factors from at least one computerized storage medium operatively connected to the computerized device. The method automatically generates questions related to the problem and the evidence topics using the computerized device. The method can also receive additional questions from the user through the user interface. The method can further receive an indication of which of the factors should be ignored and which of the factors should be considered from the user through the user interface.

In response to the questions, the method automatically generates answers to the questions by referring to the factors that should be considered and to sources within the computerized storage medium using the computerized device. The method automatically calculates confidence measures of each of the answers using the computerized device. The method then displays the questions, the answers, and the confidence measures on the user interface. The method can also display how the sources contributed to the confidence measures of the answers on the user interface.

When the user identifies one of the answers as a selected answer through the user interface, the method displays details of the sources and the factors used to generate the selected answer on the user interface. The details of the sources can include annotations to the sources made by previous users working on the same or different problems. The method can receive a rating of at least one of the sources regarding how well the sources support the answers from the at least one user, through the user interface. Further, after displaying the questions, the answers, and the confidence measures, the method can receive updated factors and/or updated information from the sources using the computerized device. Then, the method automatically generates at least one updated answer based on the updated factors and updated information from the sources using the computerized device.

The method can automatically compare the answers to the updated answers to produce an update severity score for each question using the computerized device. Then, the method can display the update severity score for each of the questions on the graphic user interface. The method automatically combines the update severity score for each of the questions to produce an update priority for the subject using the computerized device. The method further automatically ranks a plurality of subjects according to their update priority using the computerized device, and displays the plurality of subjects ranked according to update priority on the graphic user interface. The method can further maintain a history of the questions, the answers, and the confidence measures.

BRIEF DESCRIPTION OF THE DRAWINGS

The embodiments herein will be better understood from the following detailed description with reference to the drawings, which are not necessarily drawing to scale and in which:

FIG. 9 is a screenshot produced by embodiments herein;
FIG. 11 is a screenshot produced by embodiments herein.

DETAILED DESCRIPTION

DeepQA-based technology provides users with a new tool for investigating problems. The embodiments herein provide a DeepQA system and method and are therefore sometimes referred to using the shorthand DeepQA. With systems and methods herein, users have access to a question-answering system that can contextualize a question by considering a set of problem-specific sources, hypothesize about answers to a question by drawing from a huge set of structured and unstructured sources, give confidences regarding those answers, divide those confidences into contributions from evidence falling into different dimensions, and deliver the evidence sources.

Figure 1:
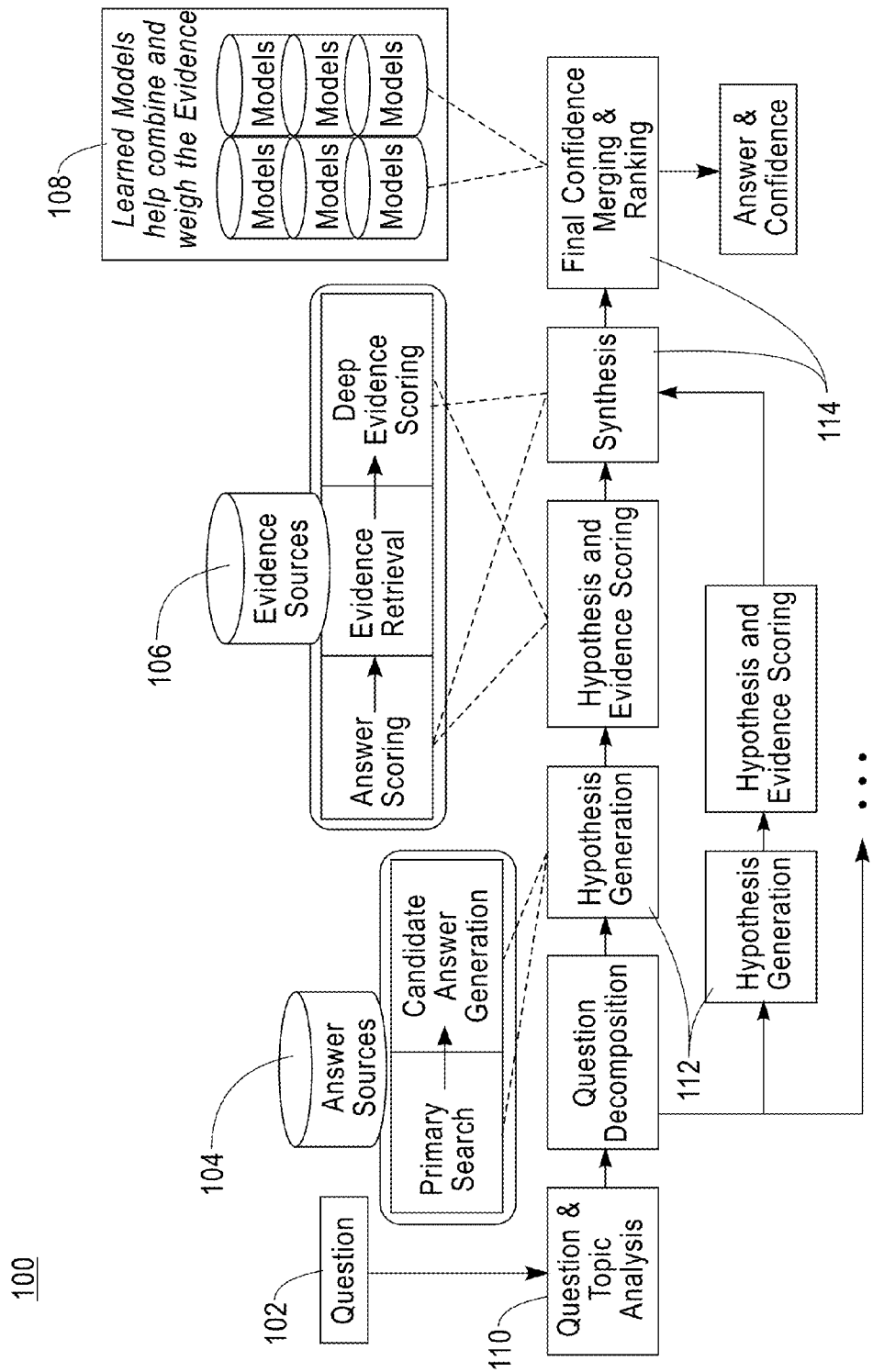
FIG. 1 is a schematic diagram illustrating system embodiments herein.

FIG. 1 illustrates one exemplary embodiment herein as a high-level view of DeepQA architecture is shown as item 100. DeepQA has a massively parallel, component-based pipeline architecture (Ferrucci, D., and Lally, A. 2004. UIMA: *An*

Architectural Approach to Unstructured Information Processing in the Corporate Research Environment. Natural Language Engineering, 10(3-4): 327-348) which uses an extensible set of structured and unstructured content sources as well as broad range of pluggable search and scoring components that allow integration of many different analytic techniques. Machine-learning is used to learn the weights for combining scores from different scorers. Each answer is linked to its supporting evidence 106. DeepQA is informed by extensive research in question answering systems (Clarke, C., Cormack, G., and Lynam, T. *Exploiting Redundancy in Question Answering*, In proceedings of SIGIR, 2001; Moldovan, D., Harabagiu, S., Pasca, M., Mihalcea, R., Girju, R., Goodrum, R. and Rus, V. *The Structure and Performance of an Open-Domain Question Answering System*. In Proc. of the 38th Meeting of the Association for Computational Linguistics, 2000; and Prager, J., Brown, E., Coden, A., and Radev, D.: *Question Answering by Predictive Annotation*. In Proceedings of the ACM SIGIR Conference on Research and Development in Information Retrieval, 2000). These systems analyze an input question 102 and generate and evaluate candidate answers using a variety of techniques 104. In the methods herein, DeepQA analyzes an input question 110 to determine precisely what it is asking for and generates many possible candidate answers 104 through a broad search of large volumes of content. For each of these candidate answers, a hypothesis 112 is formed based on considering the candidate in the context of the original question and topic. For each hypothesis, DeepQA spawns an independent thread 112 that attempts to prove it. DeepQA searches its content sources for evidence 106 that supports or refutes each hypothesis. For each evidence-hypothesis pair, DeepQA applies hundreds of algorithms that dissect and analyze the evidence along different dimensions of evidence such as type classification, time, geography, popularity, passage support, source reliability, and semantic relatedness. This analysis 110 produces hundreds of features. These features are then combined based on their learned potential for predicting the right answer 108. The final result 114 of this process is a ranked list of candidate answers, each with a confidence score indicating the degree to which the answer is believed correct, along with links back to the evidence.

Figure 2:
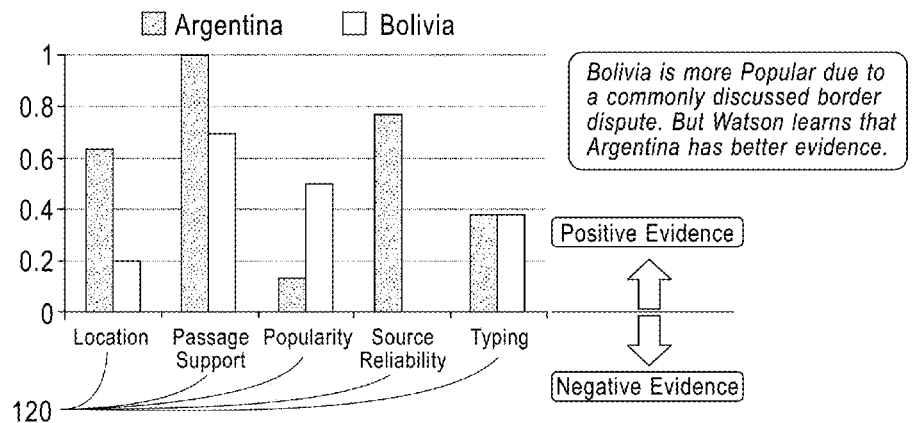
FIG. 2 is a chart illustrating functions of embodiments herein.

FIG. 2 is a chart showing the dimensions of evidence for the Jeopardy! clue "Chile shares its longest land border with this country." Each dimension 120 combines the features produced by many algorithms. Each algorithm uses different resources and algorithmic techniques, each with different precision-recall tradeoffs. To form a consumable set of evidence dimensions, features are grouped according to taxonomy of evidence types (e.g., location and popularity as shown in FIG. 2) is defined. Each dimension combines the features produced by many algorithms. Each algorithm uses different resources and algorithmic techniques, each with different precision-recall tradeoffs. To form a consumable set of evidence dimensions, features are grouped according to taxonomy of evidence types (e.g., location and popularity as shown in FIG. 2) is defined. The features are combined and weighed according to the trained machine-learning model in order to assess and display the contribution of each evidence type in producing the final confidence score.

FIG. 2 illustrates a comparative evidence profile highlighting some of the dimensions defined for Watson. Evidence profiles were used by developers for debugging, and it is thought that they will be useful for end users in many applications to understand and explore evidence associated with a candidate answer. DeepQA for Differential Diagnosis DeepQA's approach to Jeopardy! and the success of Watson suggest a powerful new architecture for reasoning over unstructured content. Traditional expert systems use forward reasoning that follows rules from data to conclusions or backward reasoning that follows rules from conclusions to data. To build these systems hand-crafted IF-THEN rules for every bit of domain knowledge are manually developed and maintained by skilled engineers or domain experts. An example of a rule taken from the Mycin system is: IF: The stain of the organism is grampos and the morphology of the organism is coccus and the growth conformation of the organism is chains, THEN: There is suggestive evidence (Clarke, C., Cormack, G., and Lynam, T. Exploiting Redundancy in Question Answering, In proceedings of SIGIR, 2001) that the identity of the organism is streptococcus.

As a result, expert systems are costly and difficult to develop and maintain as new knowledge is discovered. Expert systems are also brittle, because the underlying reasoning engine requires a perfect match between the input data and the existing rule forms. Additionally, not all rule forms can be known in advance for all the forms that input data may take, which further contributes to their brittleness. In contrast to traditional Expert Systems, DeepQA exploits natural language processing (NLP) and a variety of search techniques to analyze unstructured information to generate likely candidate answers in hypothesis generation (analogous to forward chaining). In evidence collection and scoring (analogous to backward chaining), DeepQA also uses NLP and search over unstructured information to find evidence for ranking and scoring answers based on natural language content. DeepQA's direct use of readily available knowledge in natural language content makes it more flexible, maintainable, and scalable as well as cost efficient in considering vast amounts of information and staying current with the latest content. What this approach lacks in hand-crafted precision using specific rules, it gains in breadth and flexibility.

In a clinical setting, for example, it can be used to develop a diagnostic support tool that uses the context of an input case, a rich set of observations about a patient's medical condition and generates a ranked list of diagnoses (differential diagnosis) with associated confidences based on searching and analyzing evidence from large volumes of content. Physicians and other care providers may evaluate these diagnoses along many different dimensions of evidence that DeepQA has extracted from a patient's electronic medical record (EMR) and other related content sources. For medicine, the dimensions of evidence 130 may include symptoms, findings, patient history, family history, demographics, current medications, and many others, as shown in the chart in FIG. 3. Each diagnosis in the differential diagnosis includes links back to the original evidence used by DeepQA to produce its confidence scores 132, 134 and supports the adoption of evidence-based medicine (EBM) "which aims to apply the best available evidence gained from the scientific method to clinical decision making" (Evidence-Based Medicine http://en.Wikipedia.org/wiki/Evidencebased_Medicine).

When the answers provided by DeepQA are diagnoses of the underlying causes of problems, as in the case of medical diagnosis, then the DeepQA architecture can be thought of as implementing a form of abductive reasoning (Peirce, C. S. (1901). *Abduction and induction*. In Buchler, J. (Ed.), Philosophical writings of Peirce. Mineola, N.Y.: Dover).

As a simple example of abduction, suppose that some piece of structured or unstructured knowledge in the system represents that patients with disease D have symptom S. Then, if the input to the system is that the patient has symptom S, the system will generate the hypothesis that the patient has disease D. The system will then look for evidence to support or refute this hypothesis. For a more complex example of abduction, consider that the system has numerous pieces of knowledge about diseases and their symptoms. Then, given the input that the patient has some set of symptoms, the system's task is to find the best explanation of those symptoms in terms of one or more diseases. The DeepQA architecture does this by generating hypotheses and then, in parallel, evaluating how much evidence supports each hypothesis. In effect, DeepQA is a massive abduction machine.

The use of abduction for medical diagnosis has a long history in the field of artificial intelligence. People proposed applying abduction to medical diagnosis and provided algorithms for computing explanations of data (like symptoms) in the context of a collection of axioms (medical knowledge) (Pople, H. E. (1972). *On the mechanization of abductive logic*. Proceedings of the Third International Joint Conference on Artificial Intelligence, pp. 147-152). Goebel, Furukawa, and Poole presented algorithms for generating diagnoses given medical axioms of the form disease ⊃ symptom (Goebel, R., Furukawa, K., & Poole, D. (1986). *Using definite clauses and integrity constraints as the basis for a theory formation approach to diagnostic reasoning*. Proceedings of the Third International Conference on Logic Programming, pp. 211-222). They further proposed the use of probabilistic logic for preferring one diagnosis over another. They discuss the addition of a probability to disease ⊃ symptom axioms (sensitivity). Console, Portinale, and Dupré presented an extensive formalization of abductive diagnosis and provided a method for improving the efficiency of solving abduction problems by precompiling knowledge (Console, L, Portinale, L., & Dupré, D. T. (1996). *Using compiled knowledge to guide and focus abductive diagnosis*. IEEE Transactions on Knowledge and Data Engineering. 8(5), 690-706).

Figure 3:
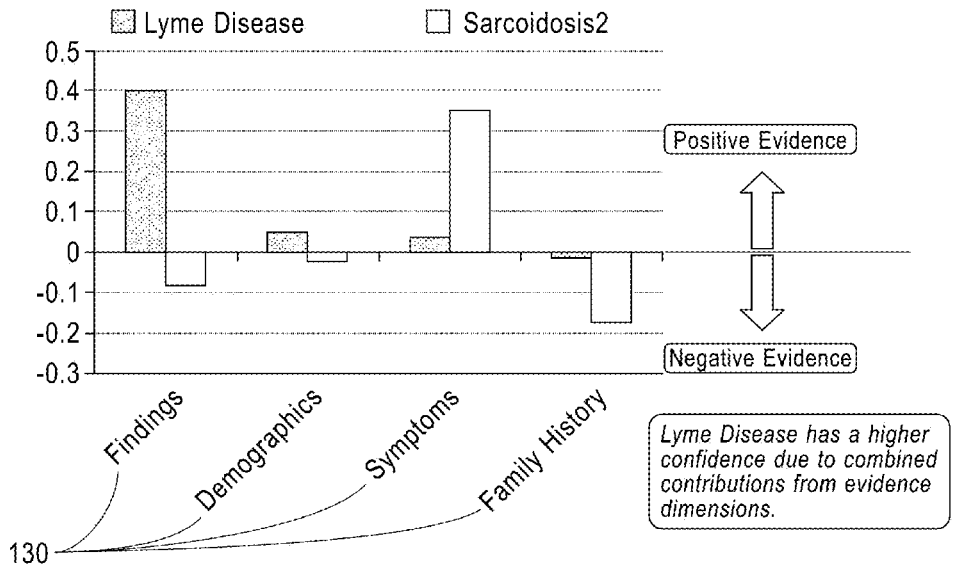
FIG. 3 is a chart illustrating functions of embodiments herein.

FIG. 3 shows a proposed set of clinical dimensions of evidence 130 of a patient with a chief complaint of eye pain and inflammation, blurred vision, headache, fever, and circular rash. Each dimension of evidence-findings 130, demographics, symptoms, and family history, aggregates individual pieces of evidence. A healthcare provider can observe the contribution of each dimension of evidence 130, as well as drill down into a particular dimension to see the contributing pieces of evidence and provenance information. Accessing this information would help refine their thinking in an evidence-based manner. The ability to explore alternative hypothesis (diagnoses), along with the confidence values and associated supporting evidence is a differentiating feature of DeepQA compared to previous systems.

This general view of DeepQA, as architecture for building lower cost, more flexible expert-system technology over readily available knowledge, led the system to consider applications beyond Jeopardy! and specifically to healthcare. One instance of IBM Journal of Research and Development was devoted to providing a detailed technical description of the Watson system and the underlying DeepQA architecture (*Deep Q&A: What is Watson?* IBM Journal of Research and Development, Vol. 56, No. 3&4, 2012 (scheduled for publication in March, 2012). The systems herein motivate the application of DeepQA to healthcare, specifically in clinical decision support. The methods herein discuss the first steps. The methods herein took to adapt DeepQA to the medical domain and how evidence profiles provide a powerful foundation for communicating with healthcare providers.

In the following section, this disclosure presents the problems clinicians face in diagnosis, and reviews past and current clinical decision support systems along with their strengths and weaknesses. This discussion is followed by the vision of how a system based on DeepQA can become an evidence-based decision support tool.

Motivation

Improving diagnostic accuracy and speed can directly improve quality of care in patients as well as reduce the overall cost incurred in this process by healthcare systems. Schiff (Schiff, G. D. MD, *Diagnosing Diagnosis Errors: Lessons from a Multi-institutional Collaborative project*. Cook County John H. Stroger Hospital & Bureau of Health Services, Chicago, USA, in Advances in Patient Safety (2); 255-278: 2005) reported diagnostic errors far outnumbering other medical errors by two to four times. Elstein (Elstein A S. *Clinical reasoning in medicine*. In: Higgs J, Jones M A, eds. Clinical Reasoning in the Health Professions. Woburn, ass: Butterworth-Heinemann; 1995:49-59) estimated a diagnostic error rate of about 15%, which is in line with findings in a number of autopsy studies (Kirch W, Schafii C. *Misdiagnosis at a university hospital in 4 medical eras*. Medicine (Baltimore). 1996; 75:29-40; and Shojania K G, Burton E C, McDonald K M, Goldman L. *Changes in rates of autopsy detected diagnostic errors over time*. JAMA. 2003; 289: 2849-2856). Singh and Graber [Singh, H., and Graber, M. *Reducing Diagnostic Error Through Medical Home Based Primary Care Reform*, JAMA. 2010; 304(4):463-464 (doi: 10.1001/jama.2010.1035) assert that "diagnostic errors are the single largest contributor to ambulatory malpractice claims 40% in some studies) and cost approximately $300,000 per claim on average." Results published from these papers and others highlight the frequency and consequence of diagnostic error in healthcare systems today and motivate the need for approaches that can reduce them.

A recent study by Graber (Graber, M., Franklin, N., Gordon, R., *Diagnostic Error in Internal Medicine*. Dept of Veterans Affairs Medical Center, Northport, N.Y. Arch Intern Med. 2005; 165:1493-14990) reviews literature related to the causes of diagnostic error and discusses results obtained in a study of 100 "error cases." They report that 65% of these cases had system-related causes and 75% had cognitive-related causes. System errors were "most often related to policies and procedures, inefficient processes, and difficulty with teamwork and communication, especially communication of test results."

Graber reported that cognitive errors were primarily due to "faulty synthesis or flawed processing of the available information." The predominant cause of cognitive error was premature closure, defined as "the failure to continue considering reasonable alternatives after an initial diagnosis was reached." Graber additionally identified four more major contributors to the cognitive errors: faulty context generation, misjudging the salience of a finding, faulty detection or perception, and failed use of heuristics.

Graber concluded that the cognitive errors "overwhelmingly reflect inappropriate cognitive processing and/or poor skills in monitoring one's own cognitive processes (metacognition)" and suggested 1) "compiling a complete differential diagnosis to combat the tendency to premature closure," 2) using the "crystal ball experience: The clinician would be told to assume that his or her working diagnosis is incorrect, and asked, What alternatives should be considered?" and 3) augmenting "a clinician's inherent metacognitive skills by using expert systems." In a recent paper, Singh and Graber also noted that "clinicians continue to miss diagnostic information . . . one likely contributing factor is the overwhelming volume of alerts, reminders, and other diagnostic information in the Electronic Health Record (EHR). Better techniques to summarize and present data are needed to enable clinicians to find the proverbial 'needle in the haystack' in the midst of voluminous data."

To compound these problems, published medical information is growing and changing extremely quickly, making the information difficult for the healthcare professional to read, process, and remember. Many emergency medical or critical situations require very rapid assessment, and correct and timely action. These challenges require mentally weighing many variables and exploring alternatives rapidly, which contributes to the cognitive overload inherent in many aspects of this practice.

The vision for DeepQA is motivated by the problems and suggested solution outlined above. The approach is to provide a decision support tool that will help the physician overcome the cognitive challenges described above by providing 1) the automatic extraction and presentation of relevant information from the EMR, 2) an extensive differential diagnosis with associated confidences and evidence profiles, and tooling to explore supporting evidence, and 3) a mixed initiative dialogue to suggest exploration of missing information and inform decisions based on evidence gathered from vast amounts of structured and unstructured information such as medical texts, encyclopedias, journals, and guidelines. This disclosure reviews some past and current medical diagnostic systems as a backdrop for a discussion of system related issues and a comparison with the approach.

Review of Medical Diagnostic Systems.

Diagnosis systems can be classified into systems that use structured knowledge, systems that use unstructured knowledge, and systems that use clinical decision formulas, rules, trees, or algorithms.

Diagnosis Systems Using Structured Knowledge.

The earliest diagnosis systems used structured knowledge or classical, manually constructed knowledge bases. The Internist-I system developed in the 1970s used disease-finding relations and disease-disease relations, with associated numbers such as sensitivity, the fraction of patients with a disease who have a finding (Myers, J. D. *The background of INTERNIST-I and QMR*. In Proceedings of ACM Conference on History of Medical Informatics (1987), 195-197). The MYCIN system for diagnosing infectious diseases, also developed in the 1970s, used structured knowledge in the form of production rules stating that, if certain facts are true, then one can conclude certain other facts with a given certainty factor (Buchanan, B. G. and Shortliffe, E. H. (Eds.) *Rule-Based Expert Systems: The MYCIN Experiments of the Stanford Heuristic Programming Project*. Addison-Wesley, Reading, M A, 1984). DXplain, developed starting in the 1980s, used structured knowledge similar to that of Internist-I, but added a hierarchical lexicon of findings (Barnett, G. O., Cimino, J. J., Hupp, J. A., Hoffer, E. P. DXplain: *An evolving diagnostic decision-support system*. JAMA 258, 1 (1987), 67-74). The Iliad system developed in the 1990s added more sophisticated probabilistic reasoning. Each disease has an associated a priori probability of the disease (in the population for which Iliad was designed) and list of findings along with the fraction of patients with the disease who have the finding (sensitivity) and the fraction of patients without the disease who have the finding (1—specificity) [Warner, H. R., Haug, P., Bouhaddou, O., Lincoln, M., Warner, H., Sorenson, D., Williamson, J. W. and Fan, C. *ILIAD as an expert consultant to teach differential diagnosis*. In Proc. Annu. Symp. Comput. Appl. Med. Care. (1988), 371-376).

Diagnosis Systems Using Unstructured Knowledge

In 2000, diagnosis systems using unstructured knowledge started to appear. These systems use some structuring of knowledge as well. For example, entities such as findings and disorders may be tagged in documents to facilitate retrieval. ISABEL uses Autonomy information retrieval software and a database of medical textbooks to retrieve appropriate diagnoses given input findings (Ramnarayan, P., Tomlinson, A., Rao, A., Coren, M., Winrow, A. and Britto, J. ISABEL: *A web-based differential diagnostic aid for pediatrics: Results from an initial performance evaluation*. Archives of Disease in Childhood 88, 5 (2003), 408-413). Autonomy Auminence uses the Autonomy technology to retrieve diagnoses given findings and organizes the diagnoses by body system (Autonomy Auminence http://www. Autonomy health.com). First CONSULT allows one to search a large collection of medical books, journals, and guidelines by chief complaints and age group to arrive at possible diagnoses (First CONSULT http://www.firstconsult.com). PEPID DDX is a diagnosis generator based on PEPID's independent clinical content (PEPID http://www.pepid.com/products/ddx/).

Diagnosis Systems Using Clinical Rules

Clinical decision rules have been developed for a number of disorders, and computer systems have been developed to help practitioners and patients apply these rules. The Case-Walker system uses a four-item questionnaire to diagnose major depressive disorder (Cannon, D. S. and Allen, S. N. *A comparison of the effects of computer and manual reminders on compliance with a mental health clinical practice guideline*. Journal of the American Medical Informatics Association 7, 2 (2000), 196-203). The PKC Advisor provides guidance on 98 patient problems such as abdominal pain and vomiting (PKC Advisor http://www.pkc.com/software/advisor/index.aspx).

Strengths and Limitations of Current System

The strengths of current diagnosis systems are that they can improve clinicians' diagnostic hypotheses [Friedman, C. P., Elstein, A. S., Wolf, F. M., Murphy, G. C., Franz, T. M., Heckerling, P. S., Fine, P. L., Miller, T. M. and Abraham, V. *Enhancement of clinicians' diagnostic reasoning by computer-based consultation: A multisite study of 2 systems*. JAMA 282, 19 (1999), 1851-1856) and can help clinicians avoid missing important diagnoses (Ramnarayan, P., Roberts, G. C., Coren, M., Nanduri, V., Tomlinson, A., Taylor, P. M., Wyatt, J. C. and Britto, J. F. *Assessment of the potential impact of a reminder system on the reduction of diagnostic errors: A quasi-experimental study*. BMC Med. Inform. Decis. Mak. 6, 22 (2006)). But, current diagnosis systems aren't widely used (Berner, E. S. *Diagnostic Decision Support Systems: Why aren't they used more and what can we do about it?* AMIA Annu. Symp. Proc. 2006 (2006), 1167-1168) for the following reasons: 1) They are not integrated into the day-to-day operations of health organizations (Coiera, E. *Guide to Health Informatics* (Second Edition). Hodder Arnold, 2003; and Shortliffe, T. *Medical thinking: What should we do?* In Proceedings of Medical Thinking: What Do We Know? A Review Meeting (2006), http://www.openclinical. org/medical Thinking 2006Summary2.html). A patient may be seen by many different healthcare workers, and patient data may be scattered across many different computer systems in both structured and unstructured form. 2) They are difficult to interact with. Entry of patient data is difficult, the list of diagnostic suggestions may be too long, and the reasoning behind diagnostic suggestions is not always transparent. 3) They aren't focused enough on next actions; they don't help the clinician figure out what to do to help the patient. They are unable to ask the practitioner for missing information that would increase confidence in a diagnosis. 4) They aren't always based on the latest, high-quality medical evidence and are difficult to keep up-to-date (Sim, I., Gorman, P., Greenes, R. A., Haynes, R. B., Kaplan, B., Lehmann, H. and Tang, P. C. *Clinical decision support systems for the practice of evidence-based medicine*. J. Am. Med. Inform. Assoc.8, 6 (2001), 527-534).

DeepQA in Healthcare

The goal with DeepQA is to address some of the weaknesses of prior approaches and to help healthcare professionals overcome the cognitive challenges they face in differential diagnosis, treatment, and other aspects of patient care outlined above. A differentiating characteristic of DeepQA is its strength in using search and NLP techniques to process knowledge present in natural language content. These techniques can be used to extract relevant information from EMRs to provide the context for solving individual cases. The same techniques used by DeepQA for Jeopardy! are adapted to generate diagnoses and treatment options and then collect evidence from huge volumes of information to support or refute those diagnoses and treatments. The ability to effectively process unstructured content found in medical resources and EMRs allows the practitioner to work with the most current knowledge available and reduces the burden associated with reading and synthesizing vast amounts of data stored in a patient record. It also helps ensure that the evidence provided in support of a set of possible solutions is readable and consumable by human users because the content is typically created by other experts in natural language rather than by knowledge engineers in formal rules.

The methods herein explain how DeepQA can be used in interaction with healthcare professionals. Physicians that were interviewed all stress the need for ease of use in medical decision support systems, especially those that are used during a patient encounter. System input must be minimal and efficient, and information provided must be unobtrusive and relevant. The goal is to minimize the input required, by automating the extraction of EMR information relevant to the current situation and providing information at a glance as new suggestions are obtained. Standing queries for diagnosis or treatment run as a background process, further minimizing the input required. A history of the practitioner's interaction with the system on a particular case provides a context for future interactions. This interaction supports system-generated suggestions as well as give practitioners the opportunity to ask directed natural language medical questions to obtain additional information they seek and will help them overcome many of the cognitive challenges discussed above, such as premature closure and faulty context generation.

Figure 7:
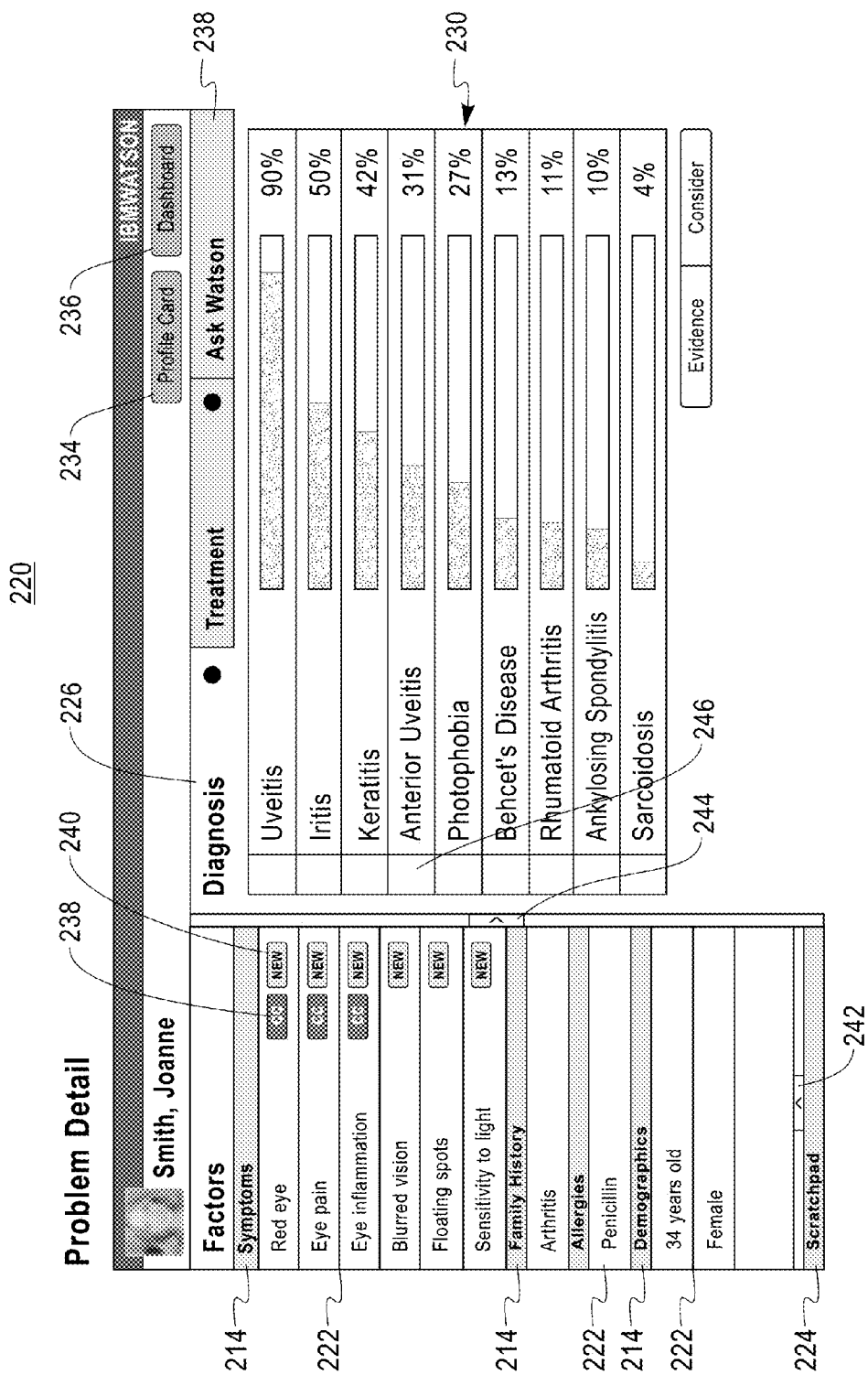
FIG. 7 is a screenshot produced by embodiments herein.
Figure 10:
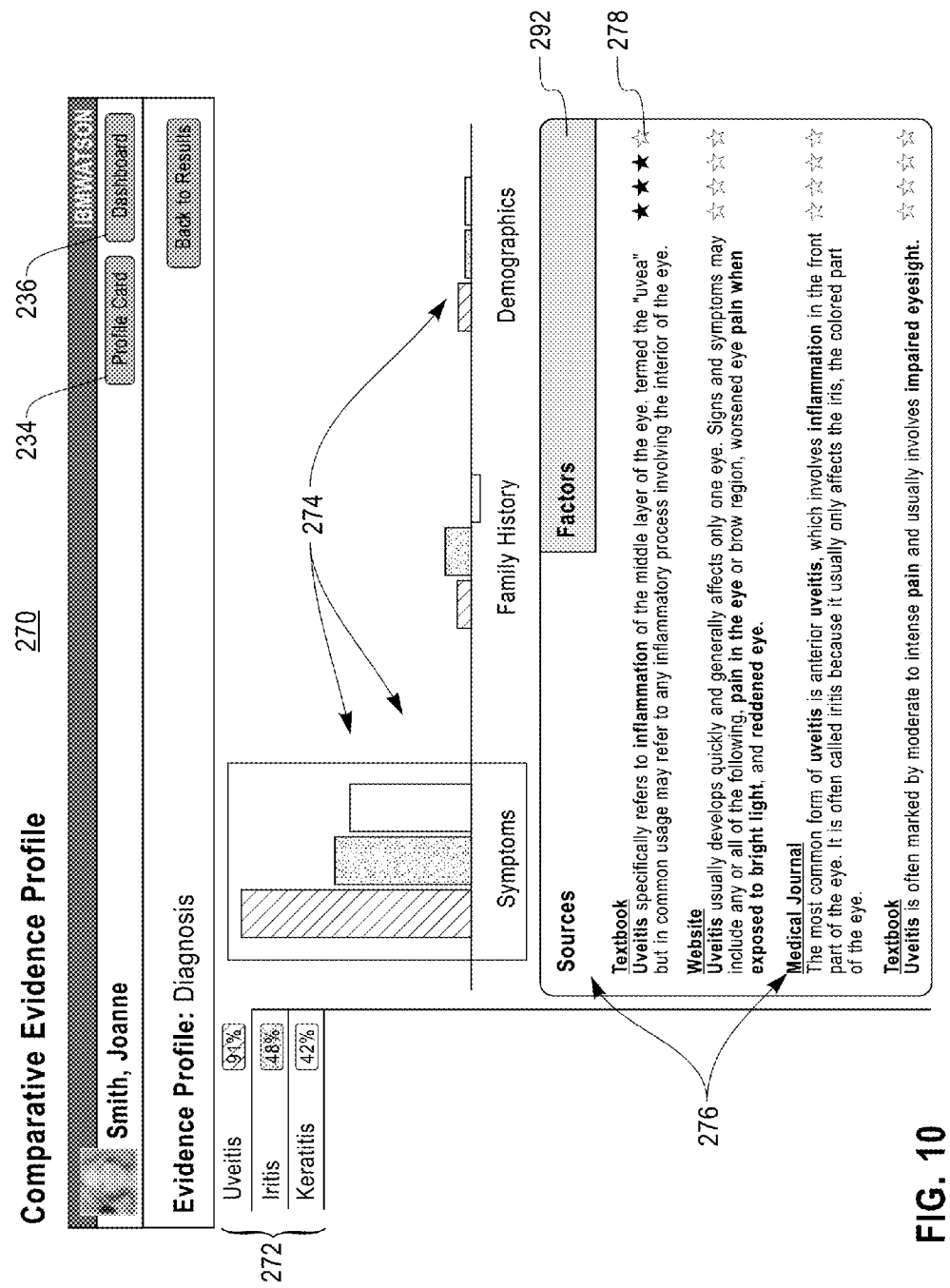
FIG. 10 is a screenshot produced by embodiments herein.

FIG. 7 illustrates a design for a user interface for clinical decision support. The left side presents information (labeled Factors 222) related to the patient's chief complaint, which would be automatically extracted from an electronic medical record (EMR). Each factor 222 is shown under its respective dimension of evidence 214, i.e., symptoms, findings, family history, and demographics. The top left side of FIG. 10 shows the current differential diagnosis 272 (only the top 3 of a long list are shown in this example) and associated confidence values for each candidate. A practitioner can select a particular candidate diagnosis. In this case, Uveitis is selected, the system explores the contribution of each dimension of evidence 274. A particular dimension (e.g. Symptoms) is selected revealing the contributing pieces of evidence as well as where they came from in the Sources tab area 276. The complete text of each source is accessible via links.

Figure 12:
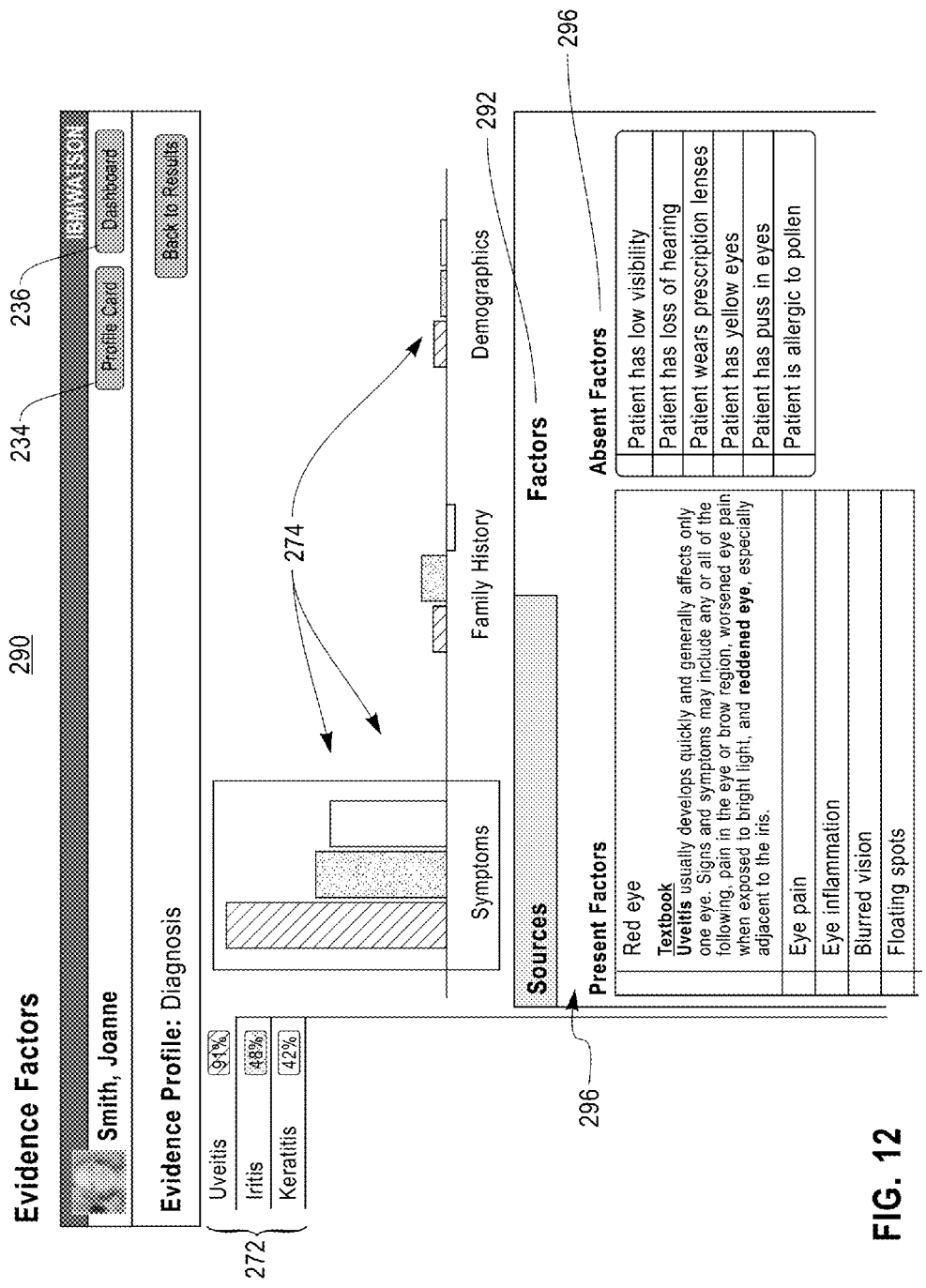
FIG. 12 is a screenshot produced by embodiments herein.

In addition, the Factors tab 292 on the bottom right in FIG. 10 may be selected to explore factors that are present as well as missing from the current case as illustrated in FIG. 12. This shows the disclosed system's ability to explore alternative hypotheses (diagnoses), along with the confidence values and associated evidence, which is another differentiating feature of DeepQA. This ability to gather evidence surrounding a hypothesis can also be used to discover information that is missing from the current clinical context and can drive mixed-initiative dialog that help clinicians gather additional information and refine their thinking in an evidence based manner. The methods herein explore this kind of information and interaction, and it is a feature of the clinical decision support system.

Research Challenges

Several challenges were addressed to apply DeepQA to clinical decision support. The methods herein divide them into the challenge of embedding the DeepQA capability into a clinical decision support system and the challenge of adapting the internal components of DeepQA to the medical domain.

The decision support system herein is able to extract relevant clinical information from EMR systems. The methods herein expect that certain portions of the clinical information such as admission notes, consults, clinical assessments, and discharge summaries will continue to be best expressed and communicated in natural language. One challenge is to apply natural language and reasoning techniques to extract, relate, and structure this information along a timeline of medical encounters.

Questions in the medical domain bring along a broader context that is described in the patient's medical history. Patient history comprises (1) a description of the chief complaint, (2) a history of the present illness, (3) a review of the major body systems, and (4) social and family history (Evaluation and Management Services Guide, Department of Health and Human Services Centers for Medicare & Medicaid Services, December 2010/ICN: 006764). Using named entity and relation annotators, the methods extract key clinical concepts that form the context for decision support. These include signs, symptoms, findings, active and past diseases, current medications, allergies, demographics, family history and many others. The concepts need to be broad enough to capture the descriptive intent of the clinician. For example, rather than just extracting "heart murmur" as a finding, the methods should also extract the related modifiers as well: "heart murmur is harsh, systolic, diamond-shaped and increases in intensity with Valsalva." Relations, for example, that indicate a specific family member had a particular disease, or that a symptom is mentioned in negation, need to be accurately captured from the language parse results. Laboratory test results need to be interpreted and evaluated for clinical significance. The extraction of this information from the patient's EMR provides context necessary for hypothesis generation and evaluation performed by DeepQA.

Significant challenges also were addressed when developing the manner in which the output of DeepQA is presented to the healthcare professionals. The clinical decision support system helps a practitioner overcome cognitive errors discussed above by explaining how a certain hypothesis was generated and what factors were considered in its evaluation. As described in the approach above, the methods herein decompose the confidence in a hypothesis into its constituent dimensions of evidence and compare them across multiple competing hypotheses so that practitioners can arrive at their own conclusions.

A useful capability to improve the quality of decision making herein is to identify the missing information about the patient that detracts from the confidence for a hypothesis, as a whole or along a specific dimension. This missing information offers a set of questions back to the healthcare professional to explore and answer. Significant opportunities for research remain in evaluating the potential informativeness of such missing information from the large amounts of information that is not recorded in a patient's EMR. When comparing across competing hypotheses, the missing information can also be evaluated and ranked according to its discriminitiveness among these hypotheses. This feedback focuses additional data gathering activities, such as diagnostic tests, to those that are more likely to confirm or reject hypotheses, sharpening the differential diagnosis in the process.

Significant areas of research were performed within the natural language processing capability of DeepQA itself. These challenges were addressed starting from DeepQA's hypothesis generation and verification components. The following section describes the efforts and their impact on medical question answering performance.

Medical Domain Adaptation

For the first phase of adaptation, the method herein obtained 5000 medical questions from the American College of Physicians (ACP). They come from a Jeopardy!-like competition, called Doctor's Dilemma, that medical interns, residents, and fellows participate in once a year. This set includes questions about diseases, treatments, lab tests, and general facts. Some examples of these questions and associated answers are: The syndrome characterized by joint pain, abdominal pain, palpable purpura, and a nephritic sediment. Answer: Henoch-Schonlein Purpura.Familial adenomatous polyposis is caused by mutations of this gene. Answer: APC Gene. The syndrome characterized by narrowing of the extra-hepatic bile duct from mechanical compression by a gallstone impacted in the cystic duct. Answer: Mirizzi's Syndrome.

The methods are currently focusing on evaluating performance on medical diagnosis questions from this set. Diagnosis questions generally describe symptoms, findings, and other contextual medical information and require a diagnosis as an answer. Thus, a good step towards differential diagnosis. Below, the methods herein report the progress in adaptation and the results of the first few experiments. Applying DeepQA to any new domain requires adaptation in three areas: 1. Content Adaptation involves organizing the domain content for hypothesis and evidence generation, modeling the context in which questions will be generated. 2. Training Adaptation involves adding data in the form of sample training questions and correct answers from the target domain so that the system can learn appropriate weights for its components when estimating answer confidence. 3. Functional Adaptation involves adding new domain-specific question analysis, candidate generation, hypothesis scoring and other components.

Content Adaptation

Content for the medical domain ranges from textbooks, dictionaries, clinical guidelines, and research articles, to public information on the web. There is often a tradeoff between reliability and the currency of information available from these content sources. By using training questions, the machine-learning models in DeepQA can learn what weight to attach to them. Alternatively, the decision maker may choose to do so manually, adjusting the confidence in a hypothesis based on its sources.

The content adaptation process navigates through the chapter and section header hierarchy of textbooks and organizes the information according to the objectives of the system. Given the focus on diagnostic support, the methods herein scan the header hierarchy for disease names and keyword variants for their causes, symptoms, diagnostic tests, and treatments. The text content in these sections is then converted into an XML format that information retrieval engines take as input for indexing. The text is further analyzed for identification of medical concepts and their semantic types according to the Unified Medical Language System terminology (UMLS http://www.ncbi.nlm.nih.gov/books/NBK9676/(version 2011AA). This extra information provides for a structured query-based lookup to complement text-based information-retrieval approaches.

The methods can supplement medical content from standard sources such as textbooks and published guidelines with knowledge available from a variety of online sources. This process of corpus expansion was developed for DeepQA. This uses existing knowledge about a concept, such as a description of symptoms for a given disease, and searches the web for similar passages. This query results in the generation of "pseudo-" documents that contain a broad range of passages that discuss various aspects of the target concept.

The methods can incorporate a modest set of medical content sources focused on internal medicine. These are ACP Medicine, Merck Manual of Diagnosis and Therapy, PIER (a collection of guidelines and evidence summaries), and MKSAP (a study guide from ACP). These sources are complemented herein with online medical content.

The content is adapted for many purposes. Information about each disease found in these sources is extracted into "pseudodocuments." First, these are retrieved during document search and the corresponding disease is proposed as a candidate answer. Second, in passage search the entire source content is searched to find relevant passages that match the question. The passages are returned for use by candidate answer generation. Third, during the evidence scoring phase, the content is searched to see if there is textual support for a given candidate answer. Fourth, the methods herein have analyzed the content to extract associations between diseases and their symptoms, findings, and tests. This structured knowledge base is used in primary search when the methods herein encounter questions looking for a diagnosis.

Training Adaptation

DeepQA relies on machine-learning methods to determine how to weigh the contribution of the various search and scoring components in the question answering pipeline. They use a training set of questions with known correct answers. Note that the methods included both diagnosis and non-diagnosis questions in training, which showed better performance on the development set than training on the much smaller set of diagnosis questions alone.

Functional Adaptation

DeepQA defines a general set of processing steps needed in a hypothesis evidencing system as shown in FIG. 1. Conceptually, this pipeline includes analyzing and interpreting a question, searching, generating candidate hypotheses, retrieving supporting evidence, and finally scoring and ranking answers. New analytic components can be easily integrated into each of these steps to meet the requirements of a particular domain. Many of the existing components developed for the Watson core system are domain-independent and therefore reusable. New domains, however, enable new domain-specific resources such as taxonomies, collections of text for capturing knowledge, as well as domain-specific question formulations and reasoning axioms, all of which fit naturally into specific functional areas of DeepQA. This process is referred to as functional adaptation. In the following sections this disclosure outlines some of the main functional areas of DeepQA.

Adapting to Domain-Specific Taxonomies and Reasoning

A valuable type of resource in the medical domain is medical ontologies such as UMLS, which contain taxonomies MeSH and SNOMED. Medical taxonomies encode variant phrasings for the same concept (e.g. "age-related hearing loss" is equivalent to "presbycusis") as well as hyponymy relations (e.g. "pyoderma gangrenosum" is a type of "skin disease"). If the system can accurately recognize concepts, these relations may be reasoned over to better evidence hypotheses. The first task discussed below is concept detection, in which the system must accurately map from text as expressed in questions and evidence passages into the taxonomy using entity disambiguation techniques. Afterward, the methods discuss how, once detected, reasoning techniques may be applied over concepts to better score candidate answers.

Concept Detection

Named Entity Disambiguation: Accurate named entity detectors exist for the medical domain such as UMLS MetaMap (UMLS MetaMap http://www.nlm.nih.Gov/research/umls/implementation_resources/metamap.html (MetaMap version 2010). Although, as many expect, the precise terminology of medical language aids in disambiguation, it turns out there are special challenges in segmentation and disambiguation. This is evident for acronyms (e.g., Liu et al. (Liu, H., Lussier, A., Friedman, C., A study of abbreviations in the UMLS. *Proceedings of the American Medical Informatics Association Sypmosium*, (2001), 393-397) found that 54% of three letter acronyms were ambiguous considering expansions in UMLS alone) but also for terms like "hypertension" which could be interpreted as "Hypertensive disease" but also as a finding, "Hypertensive adverse event," in the UMLS taxonomy. Furthermore, proper segmentation must be used to identify the appropriate level of specificity (e.g., "carcinoma," "pancreatic carcinoma," or "non-respectable pancreatic carcinoma").

Measurement recognition and interpretation: Lab findings and other numeric measurements are critical in the medical domain. Use of these demands recognition capabilities incorporating context, for instance to identify that "22 y.o." maps to the concept, "Young Adult," or that "320 mg/dL blood glucose" maps to "Hyperglycemia." While in some cases this information may be associated with health records in structured (coded) form, that is not always the case. Furthermore, the unstructured medical knowledge sources from textbooks used to generate and score answers are not structured and represent this information only in text or tabular form. The systems herein have a rule-based annotator that identifies measurements and test results as expressed in text. Based on existing guidelines, measurements are interpreted to be normal, high, or low, and mapped using general tables to the corresponding UMLS concept.

Unary Relations Normal, high, and low values may also be expressed lexically (e.g. "elevated T4") and the methods have trained statistical classifiers (Wang C., Fan, J., Kalyanpur, A., and Gondek, D. *Relation Extraction with Relation Topics*. In Conf on Emp. Methods in Natural Language Processing, 2011) and built rule based detectors to identify cases of this. Additionally, the methods have collected a set of mapping rules to map to specific concepts in UMLS when they exist (e.g., mapping from "blood pressure is elevated" to the "Hypertension" concept). Negation may be considered a unary relation and we have adapted NegEx (Chapman, W., Bridewell, W., Hanbury, P., Cooper, G., and Buchanan, B. *A simple algorithm for identifying negated findings and diseases in discharge summaries. Journal of biomedical informatics, Vol.* 34, No. 5. (October 2001), pp. 301-310) to work with the DeepQA parser to identify concepts which are negated.

Reasoning Over Concepts Using Taxonomic Resources

Domain-specific taxonomic reasoning can be used to evidence correct hypothesis via: concept matching between question and evidence passages, type coercion of answers given the desired answer type, identifying specificity of answer, and equivalent answer merging.

Concept Term Matching: The synonymy and hyponymy encoded in taxonomies may be directly used to enhance term matching within DeepQA. Term matching is used by the DeepQA passage scorers, which attempt to justify hypotheses using unstructured content. DeepQA uses an ensemble of passage scorers with different precision/recall tradeoffs, ranging from bag-of-words and subsequence matching to techniques that align predicate argument structures between supporting text passage and question. Each passage scorer contributes a score for each hypothesis-passage pair. The passage scoring framework allows the easy integration of different term matchers, and so the methods and systems herein incorporate UMLS taxonomy matching. Type Coercion: DeepQA scores how easily a candidate answer may be "coerced" to the desired lexical answer type of the question. Typing information is available in domain taxonomies as well as extractions from domain text content. Entity disambiguation is used to map candidate answers from text into the medical taxonomies. Lexical answer types (LATs) expressed in the question (e.g. "skin condition," "cause") must also be mapped through predicate disambiguation to types in the taxonomy. While "skin condition" maps directly to concepts in MeSH and SNOMED, LATs like "cause" may map to multiple concepts via a set of predicate mapping rules the methods have collected. Once both the candidate answer and type have been mapped to concepts in the taxonomy, specialized techniques can produce scores based on ancestry and other metrics over the hyponymy tree to identify if the candidate answer is of the right type.

Answer Specificity Candidate answers may range in generality or specificity. A diagnosis to a high-level disease may not be very useful to a practitioner whereas a diagnosis to a specific disease variant have a lower probability of being correct. Consider a diagnosis of "bicuspid aortic valve" versus "heart defect." Although either may help lead the user to a useful answer, the level of specificity desired may vary for presentation to specialists or general practitioners. DeepQA includes support for identifying generic classes versus instances, and in medical adaptation the method has further added scores using the medical taxonomies to identify the level of specificity of a candidate.

Answer Merging: DeepQA uses an ensemble of candidate answer generators that generate candidate answers from passages. These candidate answers may be variants referring to the same concept. By adding an answer merger that uses taxonomies to identify variant forms, the system can merge the evidence for equivalent answers.

Adapting to Domain-Specific Text Collections

As discussed in Content Adaptation, the medical domain offers large amounts of domain-specific text. In functional adaptation, this text may be used to build new resources to be used by the system as well as to provide evaluation data for developers to diagnose new refinements necessary for the domain. This disclosure discusses two such resources the methods have constructed thus far, a Symptom KB and a LSA resource, and how they are used in the system. Then, this disclosure reviews some of the refinements developed to address particular challenges that arise in medical text.

Resources Mined Over Medical Text

Latent Semantic Analysis (Deerwester, S., Dumais, S. T., Furnas, G. W., Landauer, T. K., and Harshman, R. Indexing by latent semantic analysis. J. Am. Soc. For Inform. Science, 41, 1990) is an unsupervised technique which the methods herein use to produce a latent semantic index over the medical corpus. This index loosely captures "topics" as they occur in the corpus. Then, at answer scoring time, a LSA similarity is computed between the terms in the clue and the terms associated with the candidate answer in the LSA index.

Structured Symptom Matching: While existing medical resources representing sensitivities and specificities can produce a precise probability of a diagnosis given extracted symptoms, these can be difficult to obtain in machine-readable form and keep current and consistent. As a step in this direction, the methods herein build an unsupervised resource over the unstructured medical content, where the association between symptoms and diseases are mined to produce a corpus-derived mutual-information-based structured resource representing the informativeness of a symptom for a given condition. This resource is used within DeepQA by looking up conditions associated with extracted symptoms and adding a score for that condition based on the informativeness of the associated symptoms.

Refinements to Handle Medical Text

Multidimensional Passage Scoring: A medical question typically represents multiple factors describing correct hypotheses. If a heart murmur is described as "harsh, systolic, diamond-shaped and increases in intensity with Valsalva," each of these modifiers ("harsh," "systolic," etc.) may be considered a separate factor and its relationship to the hypothesis could be discovered in a different text passage. We added a rule-based component that segments a question into factors. Then the suite of DeepQA passage scorers is run on passages for each factor, and scores are aggregated over factors via an ensemble of rollup functions (e.g. max, average, etc.), where the functions are selected using feature selection.

Supporting Passage Discourse Chunking: In Supporting Passage Retrieval, the DeepQA system performs a passage search for relevant passages containing a candidate answer by using terms from the question and the candidate answer. Then the passages retrieved are scored for the candidate answer using passage scorers. The assumption is that the passage text retrieved is associated with the candidate answer. However, in the medical domain, this assumption is frequently violated. Frequently passages discuss the differentiation of similar presenting conditions, e.g. a passage retrieved for collagenous colitis: Collagenous colitis and lymphocytic colitis are distinguished by the presence or absence of a thickened subepithelial collagen layer. The cause of microscopic colitis syndrome is uncertain.

This passage mentions three distinct forms of colitis. While the association of symptoms with each condition can be understood from the syntactic structure, recall-based passage scorers such as bag-of-words similarity would associate the same score with any of the three colitis mentions. An immediate improvement the system implemented was to perform very simple discourse chunking based on which sentences contain the candidate. This produces a discourse-focused supporting passage for scoring alongside the full passage. In the example above, this would avoid the confusion with microscopic colitis syndrome. Of course, there remains potential confusion with respect to lymphocytic colitis, which illustrates the need for syntactic scorers and better interpretation of such structures.

By specializing to the forms of evidence available in the medical domain, the domain adaptations discussed above help to realize the vision shown in FIG. 12, wherein evidence is analyzed along medically meaningful dimensions, and where evidence passages relevant to those dimensions are used in support or refutation of hypotheses.

Experimental Results

Figure 4:
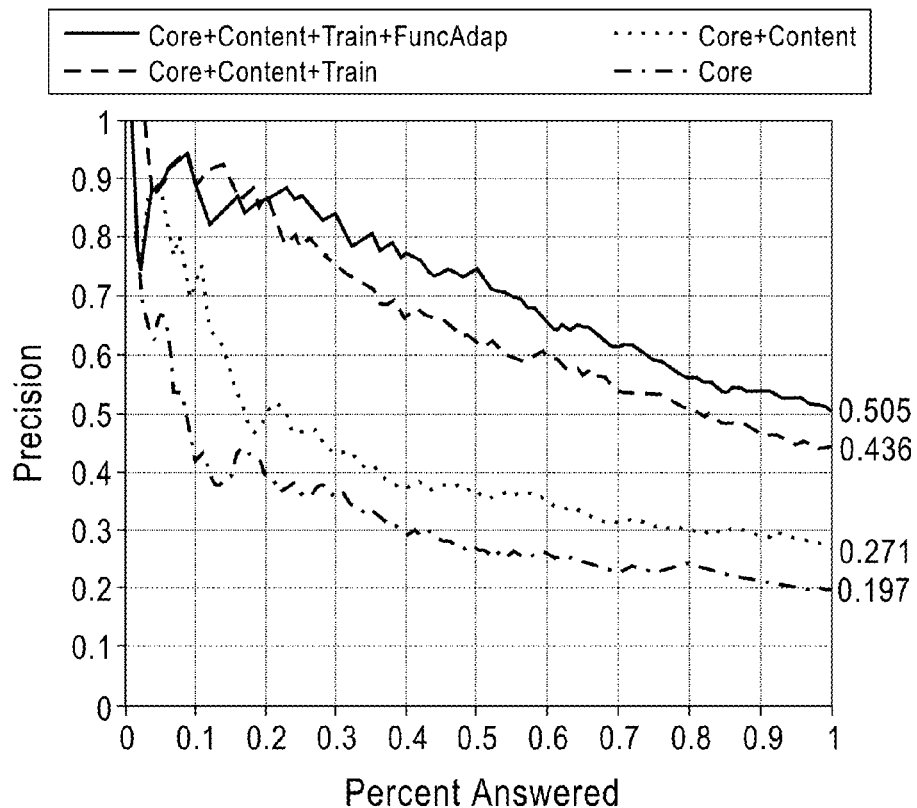
FIG. 4 is a chart illustrating functions of embodiments herein.
Figure 5:
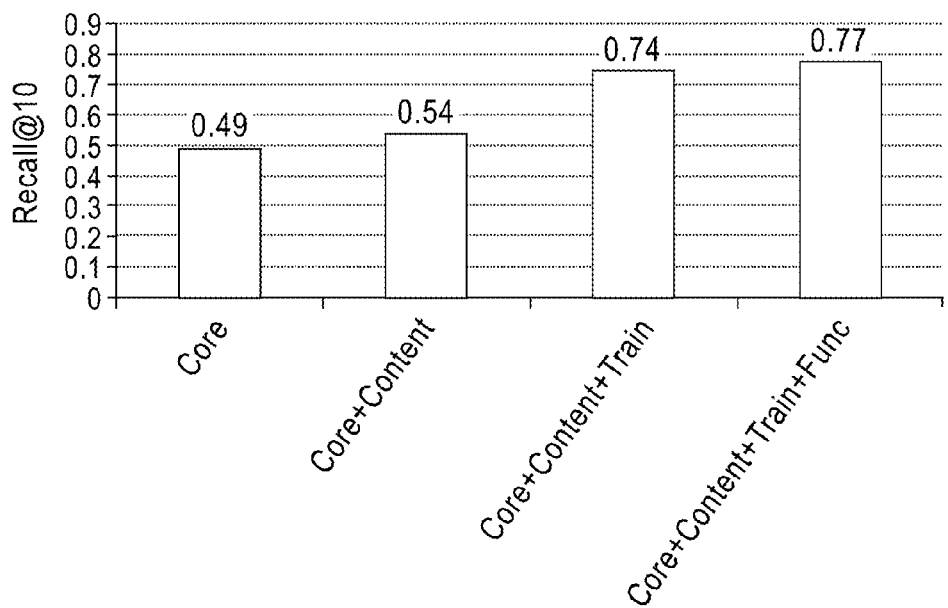
FIG. 5 is a screenshot produced by embodiments herein.

FIGS. 4 and 5 show the performance of subsequent stages of domain adaptation for the system evaluated on unseen Doctor's Dilemma diagnosis questions. FIG. 4 evaluates precision and confidence estimation only in terms of the top answer for each question. "Precision" measures the percentage of questions the system gets right for its top answer out of those it chooses to answer. "Percent answered" is the percentage of questions the system is required to answer, which it selects according to its highest estimated confidence score on the top answer. The precision at 100% answered is the "accuracy" of the system. FIG. 5 shows the "Recall@ 10" which is the percentage of questions for which the correct answer appears in the top 10 ranked answers. This metric can be a more useful target for consideration within decision support settings (e.g., differential diagnosis), where a user may further and interactively evaluate top answers from the system.

The methods display performance after each stage of domain adaptation. Core demonstrates the baseline performance of applying the core DeepQA system, with general-purpose content and models trained on Jeopardy! questions, directly to the Doctor's Dilemma set. With an accuracy of 19% and recall@ 10 of 49%, the core system shows a reasonable capability to apply to new domains, especially considering that a wide range of specialized medical content published in textbooks, journals and many other sources was not present. Core+Content shows the baseline system with medical content adaptation but Jeopardy!-trained models, which results in a 7% increase in accuracy and a 5% improvement in recall@ 10. The largest improvement was obtained by training adaptation, using 1322 Doctor's Dilemma questions for training in Core+Content+Train, which shows an additional 16% jump in accuracy and a 20% improvement in recall@ 10. Finally, Core+Content+Train+Function shows a 7% improvement in accuracy and a 3% improvement in recall@10.

Although the largest improvement was due to introducing domain-specific training, these show that the training appears to be saturating and the system will not likely show large gains from the addition of more training data. Instead, improvements depend largely on functional adaptation, which brings its own challenges. Firstly, the general-purpose NLP components included in the core system perform at a respectable level, so that the domain-specific adaptations improve performance for those aspects that existing components do not currently handle. Second, functional adaptation is a more intensive and difficult process requiring improvements in domain specific NLP and leveraging medical resources.

It is important to note that a Watson-based clinical decision support system has very different requirements than the Watson system that competed in Jeopardy!. Watson's task in Jeopardy! was to generate a single correct answer in response to a question and to buzz in with that answer if the answer's confidence estimate exceeded a dynamically computed threshold. Watson did this by generating a set of candidate answers (hypotheses) and then collecting and scoring evidence for each answer. The hypothesis with the most compelling evidence was selected as the best answer. In effect, the hypotheses competed within the evidence space. Watson will continue to use this paradigm in clinical decision support. But, in clinical decision support, Watson's task is to assist healthcare practitioners in evaluating a set of hypotheses. The focus shifts from getting the right answer in the top position to producing a set of likely hypotheses backed by high-quality evidence. The system shown below helps caregivers overcome the cognitive challenges they face by enabling them to interact with comparative evidence profiles and with the evidence to secure more informed decisions. The ability to easily explore evidence, and the quality of the evidence provided, are useful also. The method that uses the Doctor's Dilemma question set is just one step in adapting Watson to the medical domain. Ultimately, Watson's success is based on its ability to integrate effectively into clinical workflow, to improve quality of care, and to reduce costs.

Thus, improving diagnostic and treatment accuracy can directly impact the quality of care in patients as well as reduce the overall cost incurred by the healthcare systems. DeepQA defines a powerful new architecture for structuring and reasoning over unstructured natural language content and provides a foundation for developing decision support systems that can address many of the cognitive challenges clinicians face, as well as address some of the weaknesses of prior approaches. The methods and systems shown below applying DeepQA to extract, structure, and reason over natural language content found in medical textbooks, encyclopedias, guidelines, electronic medical records, and many other sources. This technology provides the basis for a clinical decision support tool affording valuable assistance in differential diagnosis, exploration of evidence that can justify or refute diagnoses, and mixed-initiative dialogue to help clinicians employ evidence based practice in their daily workflow.

The Watson GUI is a general-purpose user interface to the Watson evidence-supported, hypothesis-generating, decision support system. While the screenshots of the graphic user interface (GUI, which is sometimes just simply referred to as user interface (UI)) in this document show it populated with medical domain text, it need not be. Also, note that all labels are either driven by data delivered by Watson or by a message digest that is easily customized. This document describes the interface in some detail but to better understand it, the disclosure introduces several concepts used in its development.

Regarding some terminology used herein, a "problem" herein is a general term for a situation in which there are unknowns. The task of the UI is largely to get the user to a view of a problem from which they can explore various hypotheses and view supporting evidence. In the medical domain, a problem might be to find the unknown diagnosis that explains a patient's condition. The UI allows the user to investigate one problem at a time.

A "process of investigation and solution" herein is a codification of the steps an investigator might go through to solve a problem in a particular domain. Generally, it may be to examine findings, hypothesize reasons, perform tests and repeat until a reason is confirmed and then to try solutions. A process results in standard questions that may be applied to a problem. In the medical domain, this may be "What diagnosis explains the patient's condition?" and "What is the treatment for this patient's confirmed diagnoses?" The UI shows the user the results of applying this process of investigation and solution to a particular problem.

"Sources" herein are the structured and unstructured inputs to the systems herein. The systems herein perform their functions based on a general corpus and a problem-specific set of inputs. Watson uses NLP techniques to identify concepts in both sets of sources that may affect its hypotheses. In the medical domain, the problem-specific set of inputs is a patient's electronic medical record and the factors may be symptoms, findings, treatments, etc. The UI exposes these and they are referred to as "factors" herein.

"Scratchpad factors" are factors being considered and affect the answers Watson hypothesizes for a question. They act as normal inputs but are specific to a user as well as the problem. The UI allows for management of a user's scratchpad factors for a particular problem.

"Standing questions" herein arise from a process of investigation and solution appropriate for a particular problem. They are automatically asked by Watson as a problem's factors are updated. The UI shows results for particular standing questions for a particular problem. Regarding "ad hoc questions" herein, the user may wish to ask custom questions of Watson. The UI provides an interface to do this.

A "question's update severity" herein is a measure from 0 to 1 of how much a set of answers changed from the last time the question was considered. It may also reflect that an answer implies a need for immediate treatment.

Regarding a "subject" here, a problem relates to a single, particular subject. A subject, though, may have multiple problems. A subject may be a corporation, a piece of software, a patient, etc. The UI uses subjects to provide a high-level view of all the user's tasks. A "user" herein is someone who is responsible for multiple subjects each of which may have multiple problems.

Figure 6:
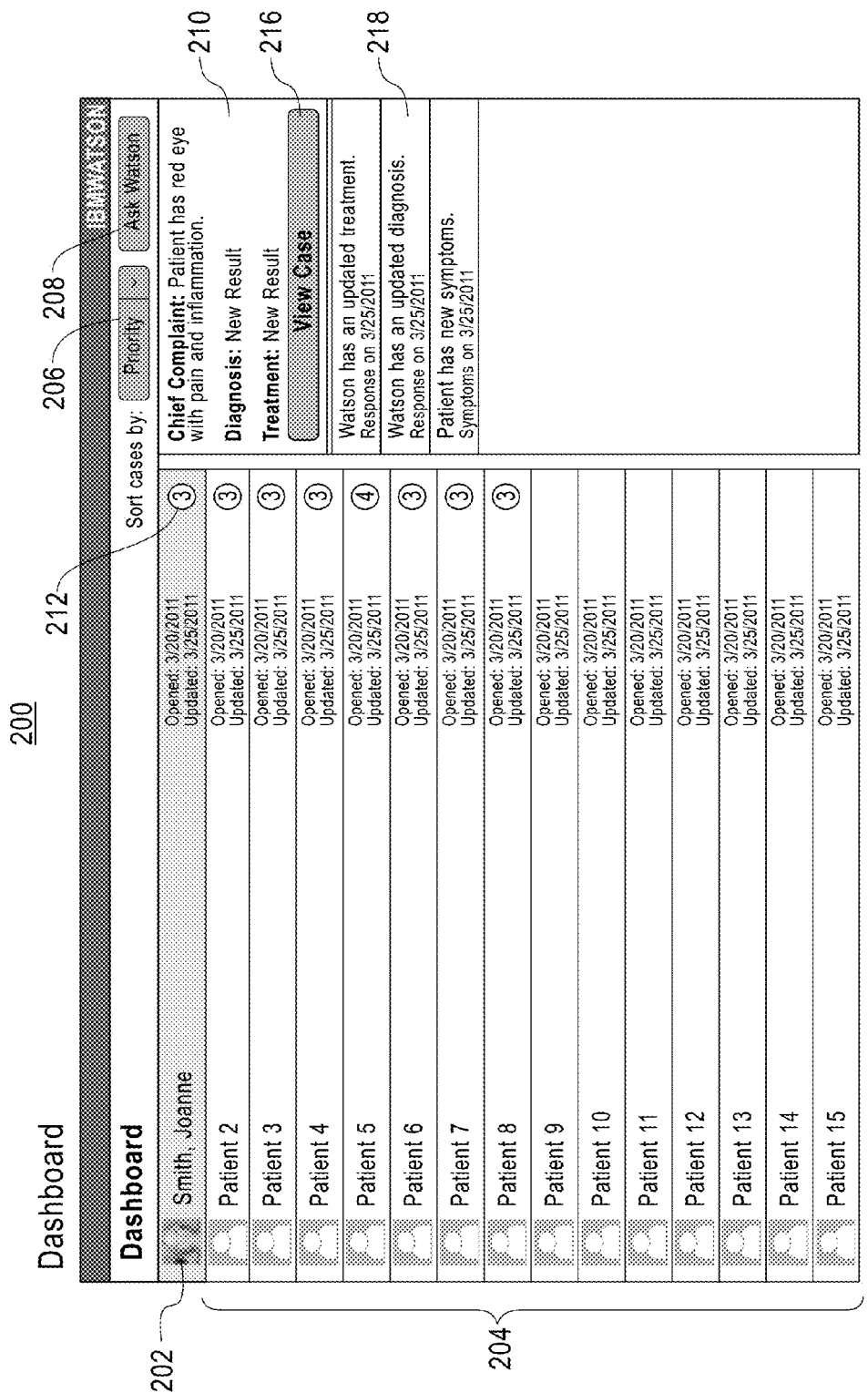
FIG. 6 is a screenshot produced by embodiments herein.

FIG. 6 shows one example of a dashboard 200. This is the "home" view of one system herein. FIG. 6 shows a summary of all the subjects 204 the user is responsible for. Subjects 204 may be ordered by title/name, update time or update priority. An update 212 is a new source addition to the problem-specific set of inputs or a new result from Watson in applying a question to a problem. "New" means it occurred since the last time the user viewed the related problem, that is, since they clicked into the problem details.

A problem's update severity (shown by colored circles 212) is simply the maximum (or some other combining function) of the update severity of all the questions it includes. Since the UI shown in the drawings uses a single problem per subject, a subject's update severity is the same as its problem's update severity in this example.

Update priority (items can be sorted by priority using button 206) is a two-dimensional measure of the subject's update severity and the number of updates. In ordering, severity is considered first and number second. In the UI, update priority is shown as a colored circle with a number inside 212. The color correlates to the severity, e.g., red as it goes to 1 and green as it goes to zero with yellow in the middle, and the number is the number of sources updated. Selecting a subject causes the right column to change to show the summary of the subject's problem (the chief complaint here) 210, updates for questions included in the problem (a "diagnosis" and a "treatment" question here) and updates to the problem-specific set of inputs.

In the screenshot 200, the list of updates 218 below the "Show Case" button 216 is showing question results and updates to individual input factors. This widget is flexible and what it displays will depend on the frequency and size of updates to visualize. For example, a coarser grain display would list the title of the sources added to the problem-specific set of inputs. The Ask Watson button 208 in the upper right allows the user to ask Watson questions outside of the context of any subject or problem.

FIG. 7 illustrates one view 220 of problem detail. The View Case button 216 takes the user to the Problem Detail 220. This view shows a particular problem for a particular subject. The subject is summarized in the header. Here, it is by a patient's picture and name. The Profile Card 234 button brings up the Profile Card. The Dashboard button 236 returns to the Dashboard. The left column lists the factors 222 Watson extracted from the problem-specific set of inputs. The categorization of the factors 222 into dimensions of evidence 214 (here, "symptoms," "family history," "allergies" and "demographics") is created by Watson using NLP techniques. Factors 222 may be tagged arbitrarily. The tags 238 are shown in blue rounded rectangles. The screenshot shows only one of these tags, "CC" for Chief Complaint. The tags are generated by the systems herein using NLP techniques.

Factors extracted from problem-specific sources added since the last time the user viewed the problem detail are marked with a green "NEW" tag 240. This is true even if the factor had been extracted from previously present sources. Note, that a factor may have been extracted from multiple sources. In each of those sources, the factor might differ lexically, e.g., "blurry vision" and "blurred eye sight." Here, the factor name is some canonical name that the systems herein assign using NLP techniques.

Clicking a factor expands it to show a single source passage that it was extracted from (see, for example, 282 in FIG. 11). As it may have been extracted from multiple sources or from multiple places in a single source, there may be many passages to choose from for display. Clicking the right-facing arrow 244 in the divider between the factors list and the questions area takes the user to the Expanded Factors view (shown in FIG. 9, discussed below). Clicking the up-facing arrow 242 in the divider between the factors list and the "SCRATCHPAD" 224 opens the Scratchpad Factors view (shown in FIG. 13, discussed below).

The tabs in the right section of the page represent standing questions (here the "Diagnosis" 226 and "Treatment" tabs) and ad hoc questions (the "Ask Watson" tab 228). The colored dots represent the question's update severity.

Within each tab's contents are the answers 230 that the systems herein have hypothesized for the question. Next to each answer is a selection checkbox 246. Selecting one or more answers and clicking "Evidence" takes the user to the Comparative Evidence Profile (shown, for example in FIG. 10). Selecting one or more answers and clicking "Consider" creates appropriate scratchpad factors for the answers. For example in the medical domain, selecting "Uveitis" and clicking "Consider" might produce the scratchpad factor "Confirmed diagnosis of Uveitis."

Figure 8:
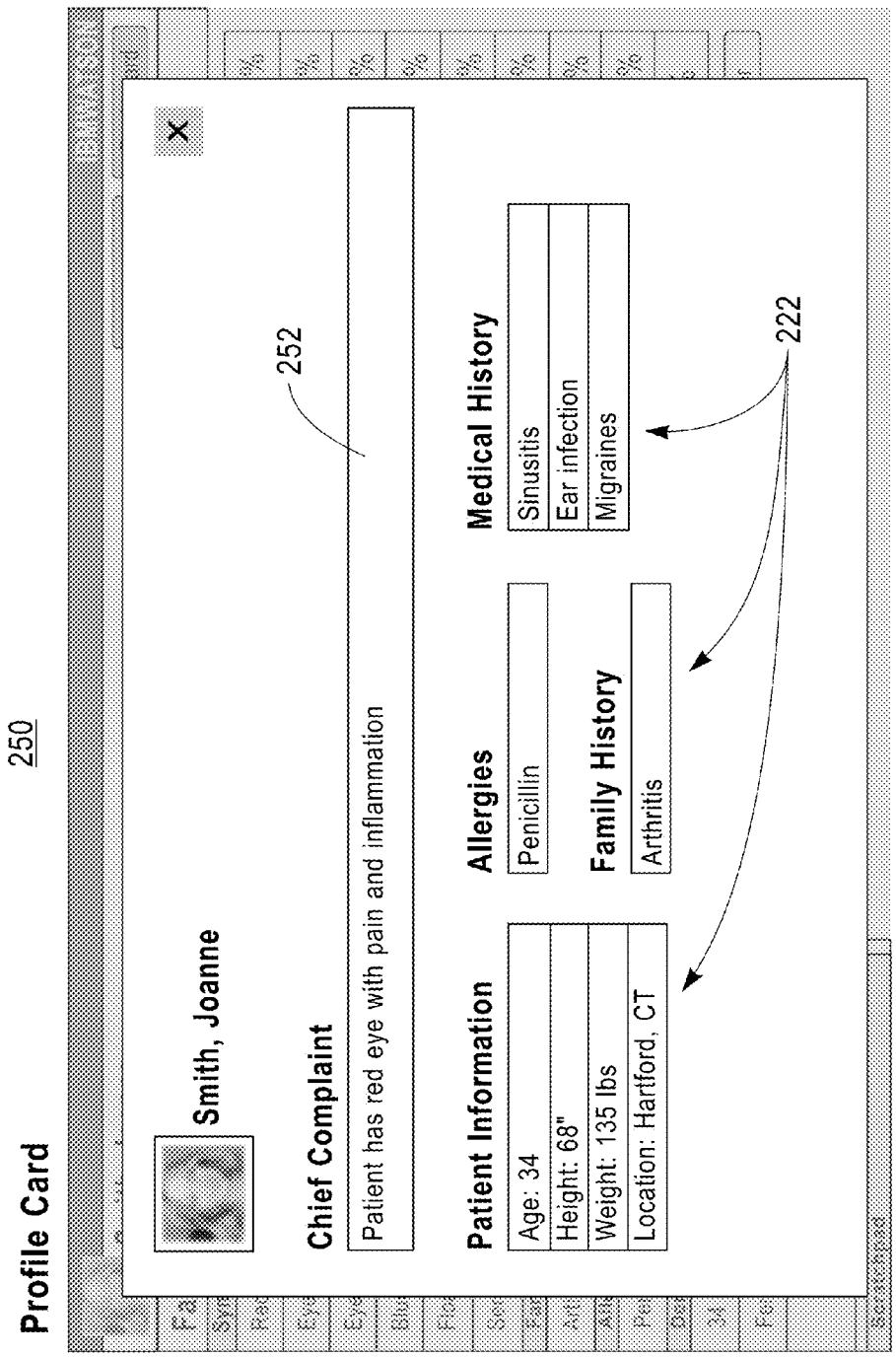
FIG. 8 is a screenshot produced by embodiments herein.

FIG. 8 shows a view 250 of a Profile Card. The profile card shows information 222 about the subject and the particular problem 252. The categories of information depend on the application as well as Watson's NLP techniques.

FIG. 9 shows a view 260 of Expanded Factors. This view lists all the factors 222 just as in the Problem Detail. Here, though, clicking a factor shows all the passages from which it was extracted in the problem-specific sources. The passages 262 are annotated to show the words in the passage that reflect the factor lexically. Clicking a passage 262 shows the full source similar to the Evidence Source Detail. The expanded view is closed by clicking the left-facing arrow in the divider at the right side of the screen shot.

FIG. 10 shows a view of Comparative Evidence Profile 270. This view shows several answers to a question. The question is shown in the header and is, here, the standing question labeled "Diagnosis." The "Back to Results" button returns to Problem Detail. In the left panel are the answers being considered. Clicking on an answer selects it. Selecting an answer causes its sources and factors 276 to be shown at the bottom of the page. Also on this page are the interleaved evidence profiles 272 for all of the answers. The evidence profile is divided into dimensions of evidence 274 (here, "Symptoms," "Family history" and "Demographics").

Within each dimension 274 are bars whose height helps to show how much of the answer's confidence (shown next to the answer in the left column) came from evidence in this dimension. Each answer gets a bar and is correlated with the answer by color. This color is saturated when its answer is selected and faded otherwise. In one example, clicking in the area of a dimension of evidence but not on a bar selects the dimension. Clicking on a bar selects the dimension and the answer. Alternatively, the interface can be established so that user does not click individual bars. Rather, the user clicks the area of the dimension of evidence to toggle it on or off and can do the same with answers. The sources and factors shown are always filtered by the selected answer and the selected dimension of evidence (if one is selected). Here then, clicking the green bar in the "Symptoms" dimension 274 would only show those sources and factors that relate Uveitis to factors categorized as "Symptoms." Clicking a source title takes the user to the Evidence Source Detail. Clicking the Factors tab takes the user to the Evidence Factors. Clicking one of the four stars 278 next to a source submits a rating of the source in terms of how well it supports the given answer given the current factors.

FIG. 11 shows a view of Evidence Source Detail 280. This view shows a source in full 282. The function of the 4 stars is described in Comparative Evidence Profile. FIG. 12 shows a view of Evidence Factors 290. This view shows the factors 292 associated with the selected answer and in the selected dimension (see Comparative Evidence Profile for selection details). Factors categorized as "present" 294 are those mentioned (either positively or negatively) in the problem-specific sources. Factors categorized as "absent" 296 are those for which no mention was found.

Figure 13:
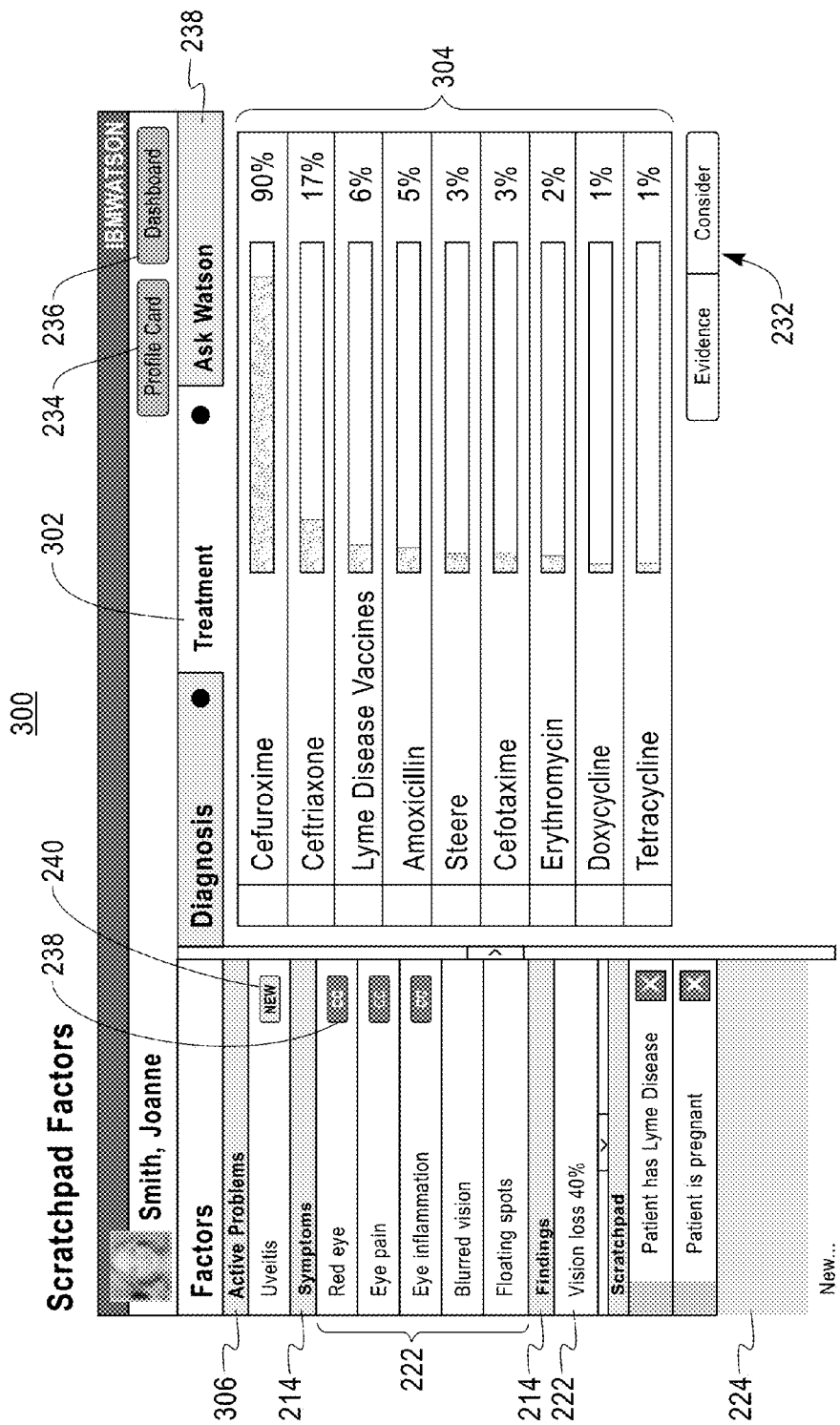
FIG. 13 is a screenshot produced by embodiments herein.

Clicking a factor's name 306 shows passages from sources that give evidence for this factor relating to the answer. Clicking a source title takes the user to the Evidence Source Detail. FIG. 13 shows a view of Scratchpad Factors 224. As shown in FIG. 12, clicking the checkbox next to an absent factor 296 adds it to the Scratchpad Factors 224. The scratchpad factors for this problem and the current user are shown in the lower left of the screen shot 224 in FIG. 13. The checkbox to the left of a factor 222 is used to enable or disable the factor when evaluating the questions. The X to the right of each factor removes the factor from the scratchpad 224. Clicking the "New . . . " area allows the user to type in free form text. Pressing enter creates a new scratchpad factor from that text.

Figure 14:
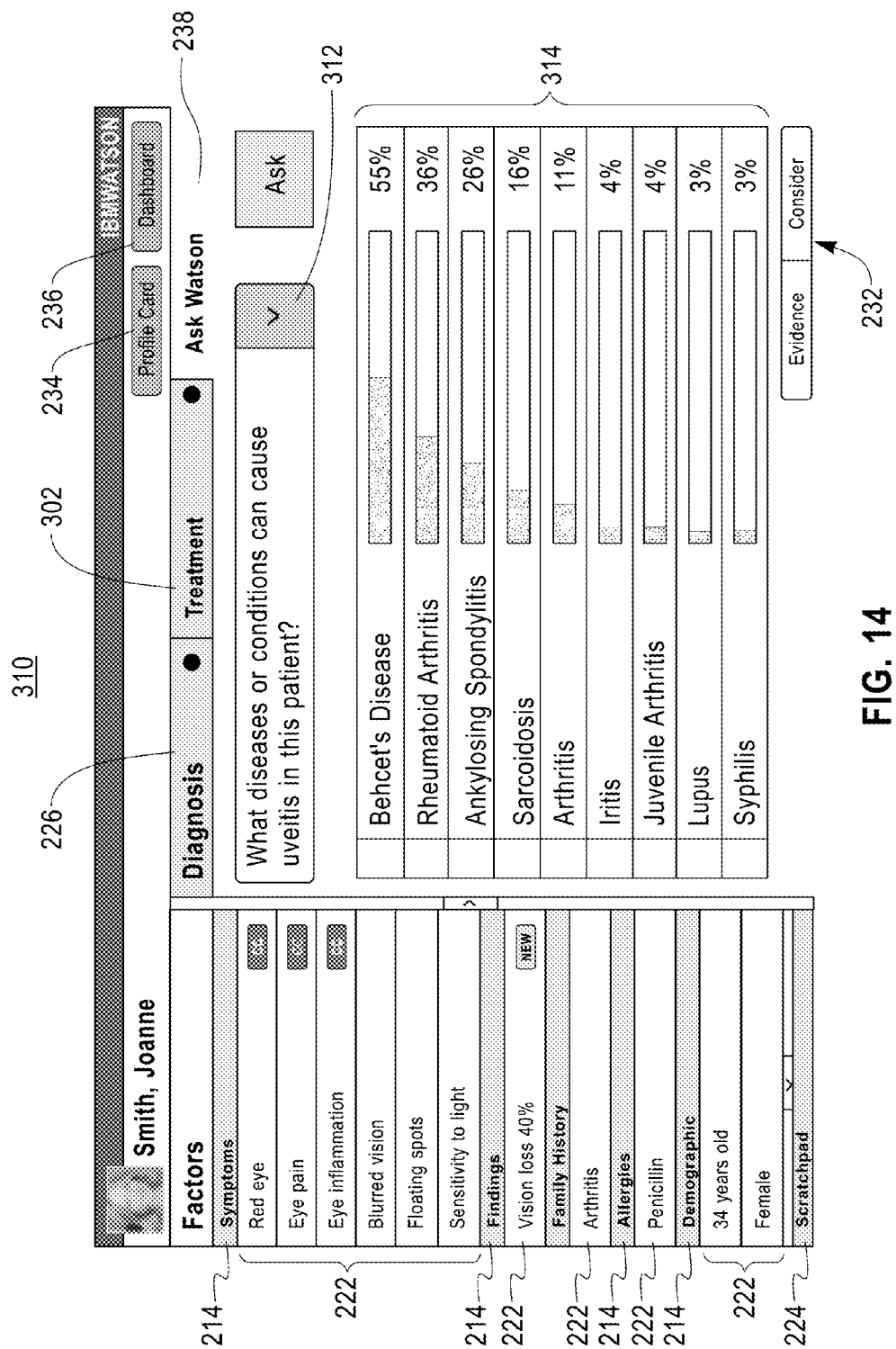
FIG. 14 is a screenshot produced by embodiments herein.
Figure 15:
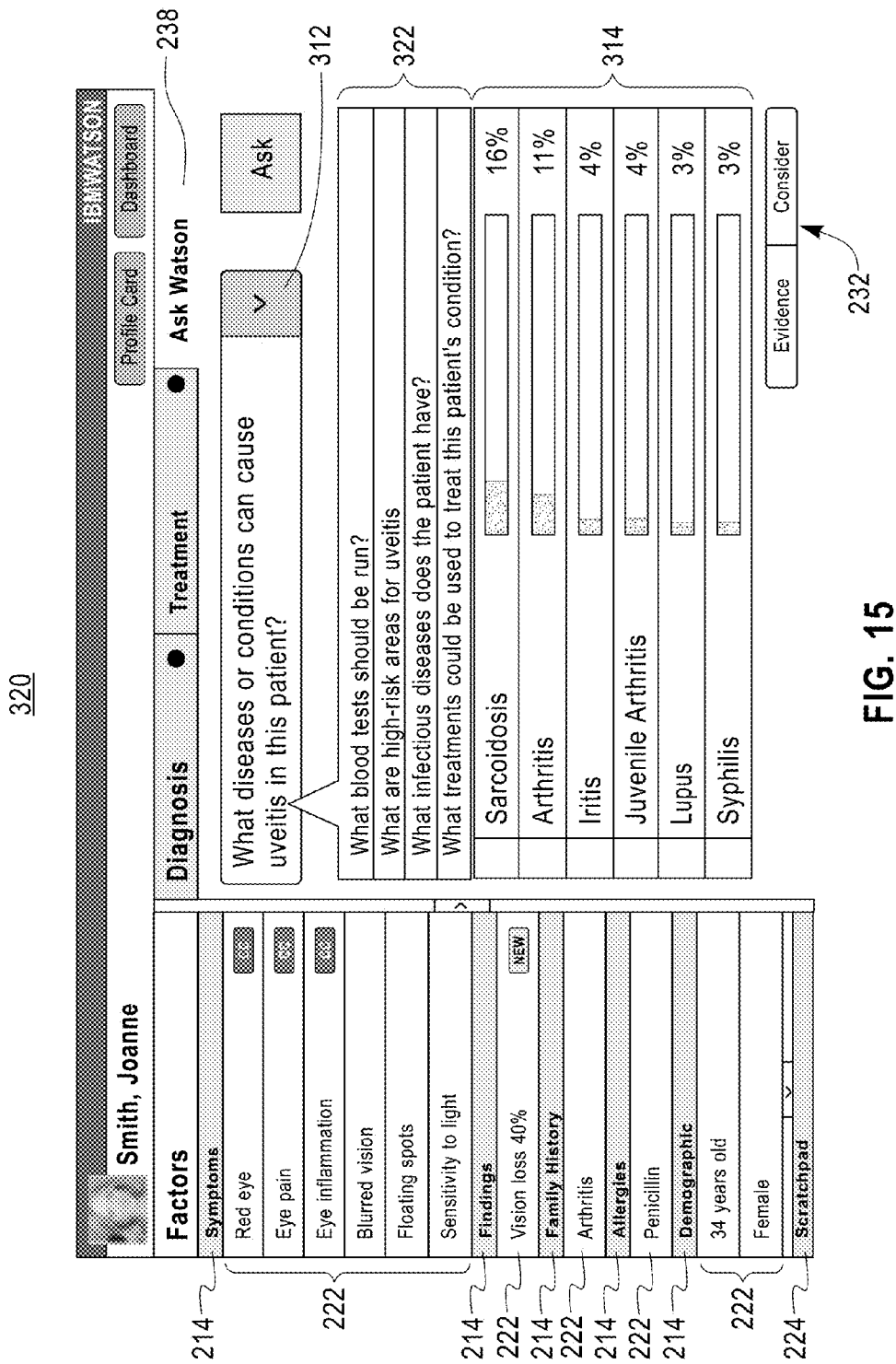
FIG. 15 is a screenshot produced by embodiments herein.

FIG. 13 is a screenshot 300 that illustrates the treatment question 302 and associated answers 304. FIG. 14 is a view of a screenshot 310 of the Ask Watson tab 228. In item 312, the user asks a question, for example "what diseases or conditions can cause uveitis in this patient?" Item 314 shows the answers to the question asked. Similarly, FIG. 15 is a view of a screenshot 320 the Ask Watson tab 228, where additional suggested questions 322 are supplied to the user automatically in response to the question presented in item 312. Selecting any of these questions 322 provides additional answers.

Figure 16:
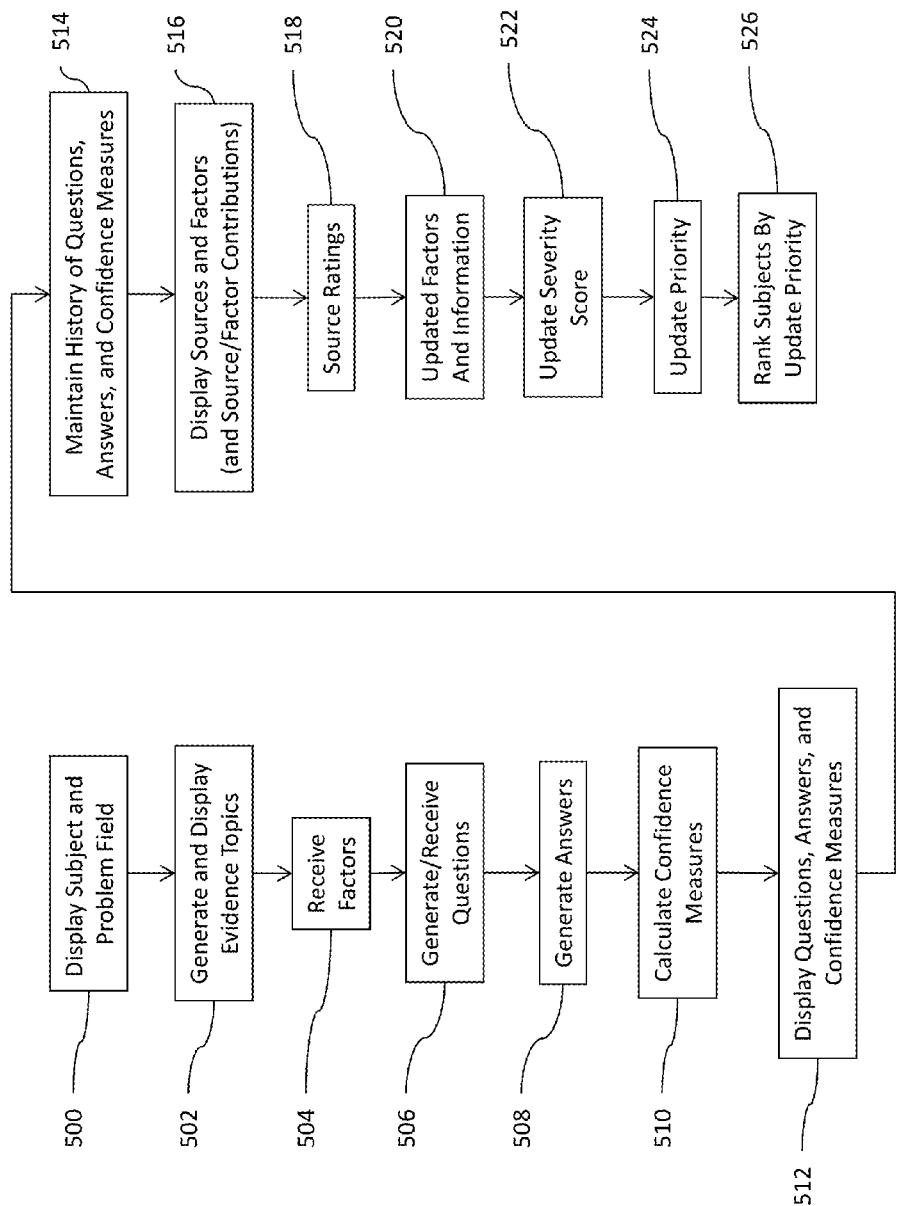
FIG. 16 is a flow diagram illustrating embodiments herein.

As shown in flowchart form in FIG. 16, an exemplary method herein displays, on a user interface in item 500, at least one subject (or allows the user to enter or select a subject) and displays a entry field location for at least one user to enter at least one problem related to the subject. The problem comprises unknown items upon which the user desires to obtain additional information, such as a question or statement, for example. In response to the problem being input by the user, in item 502, the method automatically generates evidence topics related to the problem using a computerized device operatively connected to the user interface. In some embodiments, the evidence topics can be categorized into dimensions of evidence.

Further, in item 502, the method displays the evidence topics, potentially categorized into the dimensions of evidence on the user interface. The method can receive factors in response to the evidence topics from the user through the user interface in item 504 and the method can also automatically retrieve additional factors from at least one computerized storage medium operatively connected to the computerized device. The method can further receive an indication of which of the factors should be ignored and which of the factors should be considered from the user through the user interface. The method automatically generates questions related to the problem and the evidence topics using the computerized device in item 506. The method can also receive additional questions from the user through the user interface in item 506.

In response to the questions, in item 508 the method automatically generates answers to the questions by referring to the factors that should be considered and to sources within the computerized storage medium using the computerized device. The method automatically calculates confidence measures of each of the answers using the computerized device in item 510. The method then displays the questions, the answers, and the confidence measures on the user interface in item 512. The method can further maintain a history of the questions, the answers, and the confidence measures, as shown in item 514.

When the user identifies one of the answers as a selected answer through the user interface, the method displays details of the sources and the factors used to generate the selected answer on the user interface in item 516. The method can also display how the sources and factors contributed to the confidence measures of the answers on the user interface in item 516. The details of the sources can include annotations to the sources made by previous users working on the same or different problems in item 516.

The method can receive a rating of at least one of the sources regarding how well the sources support the answers from the at least one user in item 518, through the user interface. Further, after displaying the questions, the answers, and the confidence measures, the method can receive updated factors and/or updated information from the sources using the computerized device in item 520. Then, the method automatically generates at least one updated answer based on the updated factors and updated information from the sources using the computerized device.

The method can automatically compare the answers to the updated answers to produce an update severity score for each question using the computerized and display the update severity score for each of the questions on the graphic user interface in item 522. The method automatically combines the update severity score for each of the questions to produce an update priority for the subject using the computerized device in item 524. The method further automatically ranks a plurality of subjects according to their update priority using the computerized device, and displays the plurality of subjects ranked according to update priority on the graphic user interface in item 526.

As will be appreciated by one skilled in the art, aspects of the systems and methods herein may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable non-transitory medium(s) may be utilized. The computer readable medium may be a computer readable signal medium or a computer readable storage medium. The non-transitory computer storage medium stores instructions, and a processor executes the instructions to perform the methods described herein. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments herein. It will be understood that each block of the flowchart illustrations and/or two-dimensional block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 17:
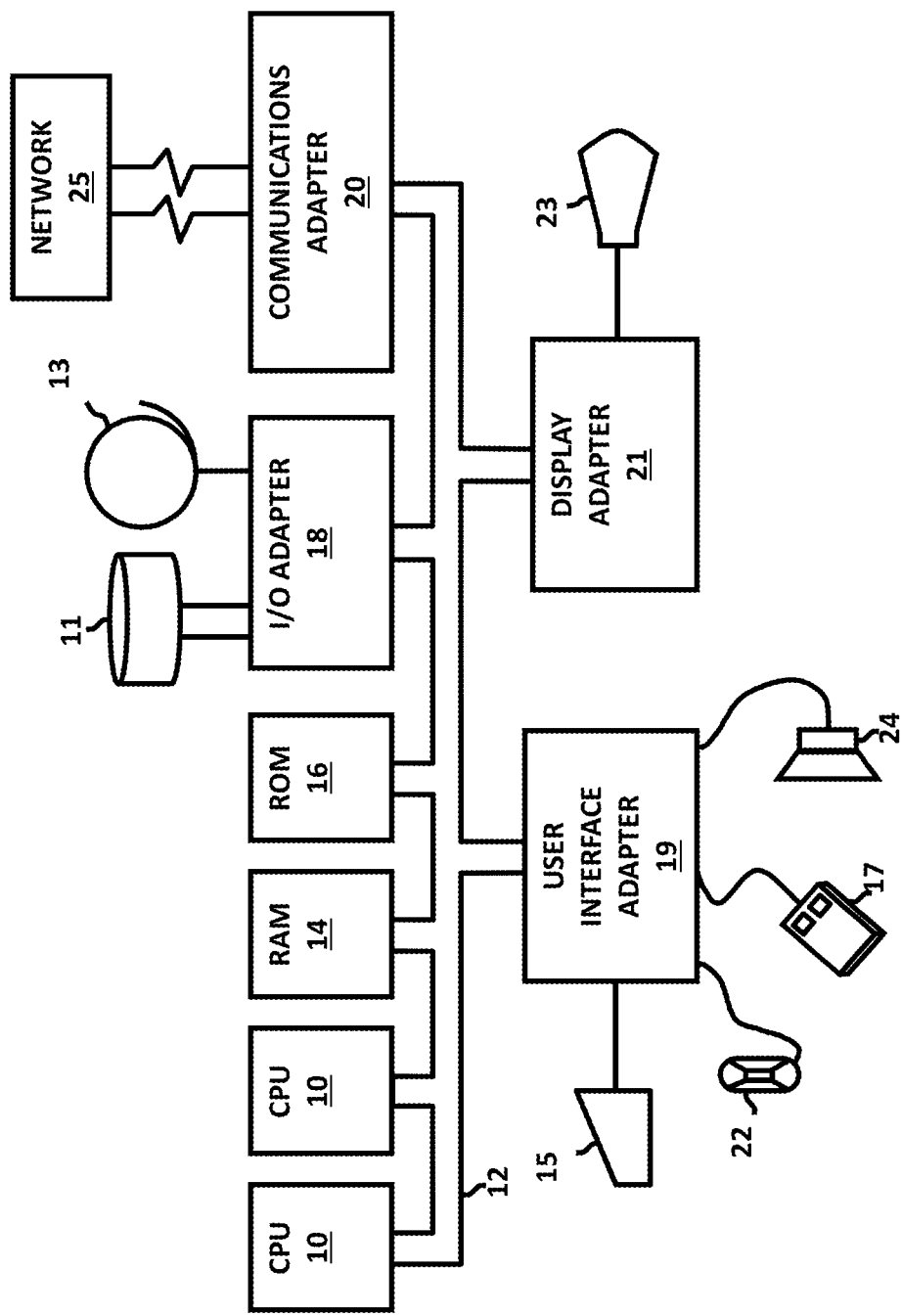
FIG. 17 is a schematic diagram of a hardware system according to embodiments herein.

A representative hardware environment for practicing the embodiments herein is depicted in FIG. 17. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The flowchart and block diagrams in the Figures illustrate the architecture, functionality, and operation of possible implementations of systems, methods and computer program products according to various embodiments herein. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Deployment types include loading directly in the client, server and proxy computers via loading a storage medium such as a CD, DVD, etc. The process software may also be automatically or semi-automatically deployed into a computer system by sending the process software to a central server or a group of central servers. The process software is then downloaded into the client computers that will execute the process software. The process software is sent directly to the client system via e-mail. The process software is then either detached to a directory or loaded into a directory by a button on the e-mail that executes a program that detaches the process software into a directory. Send the process software directly to a directory on the client computer hard drive. When there are proxy servers, the process will, select the proxy server code, determine on which computers to place the proxy servers' code, transmit the proxy servers' code, transmit the proxy server code, and then install the proxy server code on the proxy computer. The process software will be transmitted to the proxy server then stored on the proxy server.

While it is understood that the process software may be deployed by manually loading directly in the client, server and proxy computers via loading a storage medium such as a CD, DVD, etc., the process software may also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by a button on the e-mail that executes a program that detaches the process software into a directory. Another alternative is to send the process software directly to a directory on the client computer hard drive. When there are proxy servers, the process will, select the proxy server code, determine on which computers to place the proxy servers' code, transmit the proxy server code, then install the proxy server code on the proxy computer. The process software will be transmitted to the proxy server then stored on the proxy server.

Figure 18:
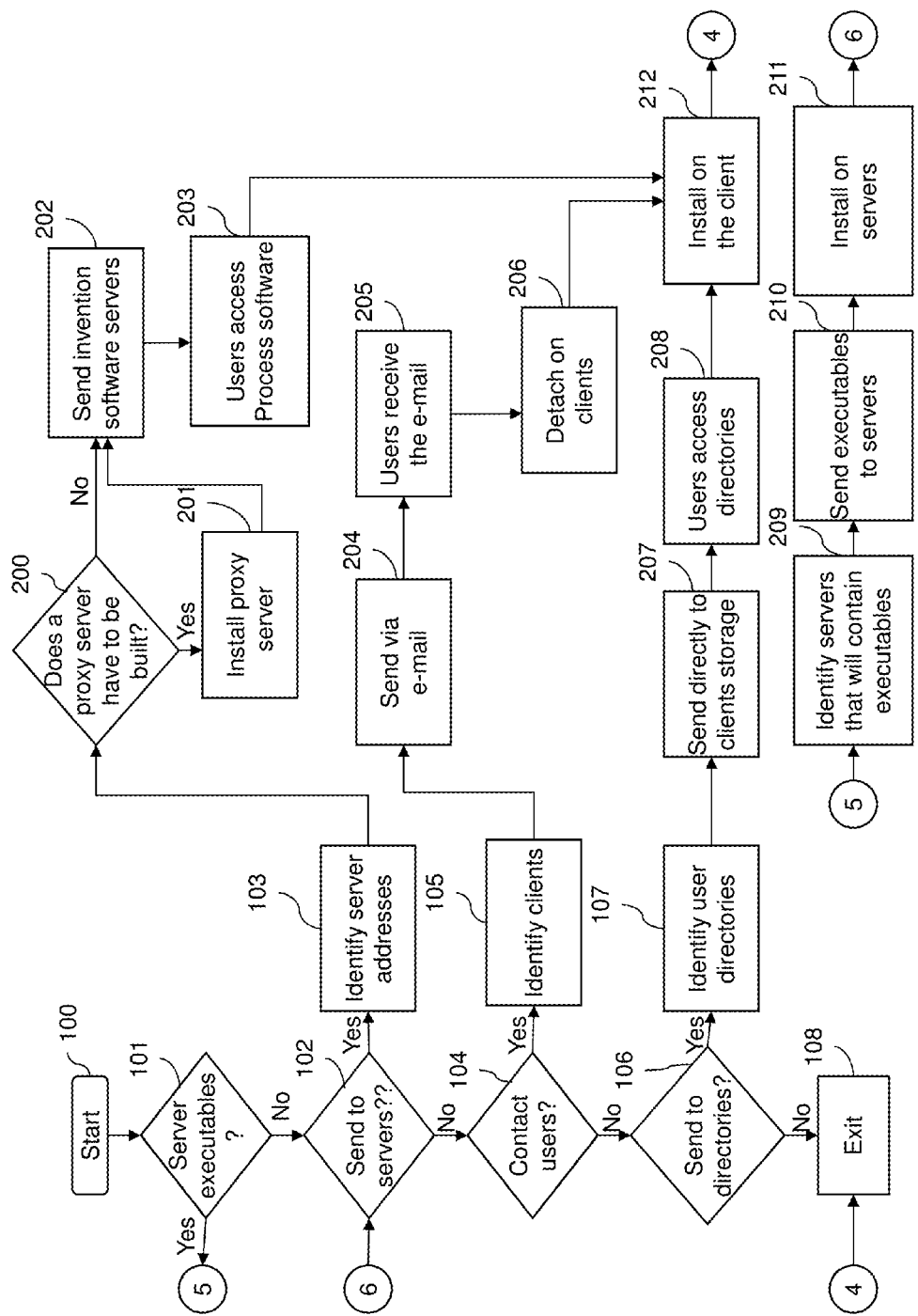
FIG. 18 is a schematic diagram of a deployment system according to embodiments herein.

In FIG. 18, Step 100 begins the deployment of the process software. The first thing is to determine if there are any programs that will reside on a server or servers when the process software is executed 101. If this is the case then the servers that will contain the executables are identified 209. The process software for the server or servers is transferred directly to the servers' storage via FTP or some other protocol or by copying through the use of a shared file system 210. The process software is then installed on the servers 211.

Next, a determination is made on whether the process software is to be deployed by having users access the process software on a server or servers 102. If the users are to access the process software on servers then the server addresses that will store the process software are identified 103.

A determination is made if a proxy server is to be built 200 to store the process software. A proxy server is a server that sits between a client application, such as a Web browser, and a real server. It intercepts all requests to the real server to see if it can fulfill the requests itself. If not, it forwards the request to the real server. The two primary benefits of a proxy server are to improve performance and to filter requests. If a proxy server is required then the proxy server is installed 201. The process software is sent to the servers either via a protocol such as FTP or it is copied directly from the source files to the server files via file sharing 202. Another embodiment would be to send a transaction to the servers that contained the process software and have the server process the transaction, then receive and copy the process software to the server's file system. Once the process software is stored at the servers, the users via their client computers, then access the process software on the servers and copy to their client computers file systems 203. Another embodiment is to have the servers automatically copy the process software to each client and then run the installation program for the process software at each client computer. The user executes the program that installs the process software on his client computer 212 then exits the process 108.

In step 104 a determination is made whether the process software is to be deployed by sending the process software to users via e-mail. The set of users where the process software will be deployed are identified together with the addresses of the user client computers 105. The process software is sent via e-mail 204 to each of the users' client computers. The users then receive the e-mail 205 and then detach the process software from the e-mail to a directory on their client computers 206. The user executes the program that installs the process software on his client computer 212 then exits the process 108.

Lastly, a determination is made on whether to the process software will be sent directly to user directories on their client computers 106. If so, the user directories are identified 107. The process software is transferred directly to the user's client computer directory 207. This can be done in several ways such as but not limited to sharing of the file system directories and then copying from the sender's file system to the recipient user's file system or alternatively using a transfer protocol such as File Transfer Protocol (FTP). The users access the directories on their client file systems in preparation for installing the process software 208. The user executes the program that installs the process software on his client computer 212 then exits the process 108.

The process software is integrated into a client, server and network environment by providing for the process software to coexist with applications, operating systems and network operating systems software and then installing the process software on the clients and servers in the environment where the process software will function.

The first step is to identify any software on the clients and servers including the network operating system where the process software will be deployed that are required by the process software or that work in conjunction with the process software. This includes the network operating system that is software that enhances a basic operating system by adding networking features.

Next, the software applications and version numbers will be identified and compared to the list of software applications and version numbers that have been tested to work with the process software. Those software applications that are missing or that do not match the correct version will be upgraded with the correct version numbers. Program instructions that pass parameters from the process software to the software applications will be checked to ensure the parameter lists matches the parameter lists required by the process software. Conversely parameters passed by the software applications to the process software will be checked to ensure the parameters match the parameters required by the process software. The client and server operating systems including the network operating systems will be identified and compared to the list of operating systems, version numbers and network software that have been tested to work with the process software. Those operating systems, version numbers and network software that do not match the list of tested operating systems and version numbers will be upgraded on the clients and servers to the required level.

After ensuring that the software, where the process software is to be deployed, is at the correct version level that has been tested to work with the process software, the integration is completed by installing the process software on the clients and servers.

Figure 19:
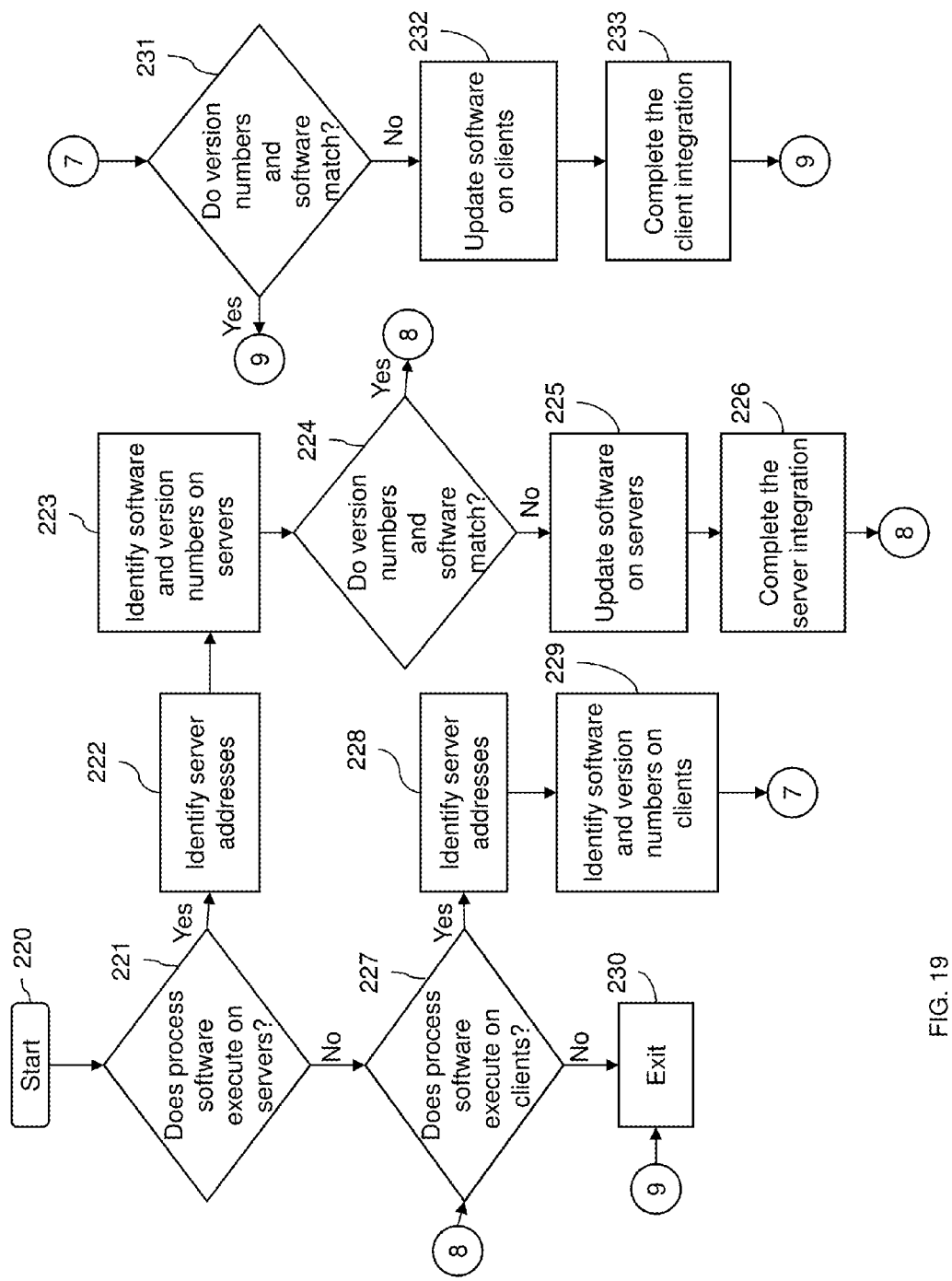
FIG. 19 is a schematic diagram of an integration system according to embodiments herein.

In FIG. 19, Step 220 begins the integration of the process software. The first thing is to determine if there are any process software programs that will execute on a server or servers 221. If this is not the case, then integration proceeds to 227. If this is the case, then the server addresses are identified 222. The servers are checked to see if they contain software that includes the operating system (OS), applications, and network operating systems (NOS), together with their version numbers, that have been tested with the process software 223. The servers are also checked to determine if there is any missing software that is required by the process software 223.

A determination is made if the version numbers match the version numbers of OS, applications and NOS that have been tested with the process software 224. If all of the versions match and there is no missing required software the integration continues in 227.

If one or more of the version numbers do not match, then the unmatched versions are updated on the server or servers with the correct versions 225. Additionally if there is missing required software, then it is updated on the server or servers 225. The server integration is completed by installing the process software 226.

Step 227 which follows either 221, 224 or 226 determines if there are any programs of the process software that will execute on the clients. If no process software programs execute on the clients the integration proceeds to 230 and exits. If this not the case, then the client addresses are identified 228.

The clients are checked to see if they contain software that includes the operating system (OS), applications, and network operating systems (NOS), together with their version numbers, that have been tested with the process software 229. The clients are also checked to determine if there is any missing software that is required by the process software 229.

A determination is made as to whether the version numbers match the version numbers of OS, applications and NOS that have been tested with the process software 231. If all of the versions match and there is no missing required software, then the integration proceeds to 230 and exits.

If one or more of the version numbers do not match, then the unmatched versions are updated on the clients with the correct versions 232. In addition, if there is missing required software then it is updated on the clients 232. The client integration is completed by installing the process software on the clients 233. The integration proceeds to 230 and exits.

The process software can be stored on a shared file system accessible from one or more servers. The process software is executed via transactions that contain data and server processing requests that use CPU units on the accessed server. CPU units are units of time such as minutes, seconds, hours on the central processor of the server. Additionally the assessed server may make requests of other servers that require CPU units. CPU units are an example that represents but one measurement of use. Other measurements of use include but are not limited to network bandwidth, memory usage, storage usage, packet transfers, complete transactions etc. When multiple customers use the same process software application, their transactions are differentiated by the parameters included in the transactions that identify the unique customer and the type of service for that customer. All of the CPU units and other measurements of use that are used for the services for each customer are recorded. When the number of transactions to any one server reaches a number that begins to affect the performance of that server, other servers are accessed to increase the capacity and to share the workload. Likewise, when other measurements of use such as network bandwidth, memory usage, storage usage, etc. approach a capacity so as to affect performance, additional network bandwidth, memory usage, storage etc. are added to share the workload. The measurements of use used for each service and customer are sent to a collecting server that sums the measurements of use for each customer for each service that was processed anywhere in the network of servers that provide the shared execution of the process software. The summed measurements of use units are periodically multiplied by unit costs and the resulting total process software application service costs are alternatively sent to the customer and or indicated on a web site accessed by the customer which then remits payment to the service provider. In another embodiment, the service provider requests payment directly from a customer account at a banking or financial institution. In another embodiment, if the service provider is also a customer of the customer that uses the process software application, the payment owed to the service provider is reconciled to the payment owed by the service provider to minimize the transfer of payments.

The process software is shared, simultaneously serving multiple customers in a flexible, automated fashion. It is standardized, requiring little customization and it is scalable, providing capacity on demand in a pay-as-you-go model.

In another embodiment, the service provider requests payment directly from a customer account at a banking or financial institution.

In another embodiment, if the service provider is also a customer of the customer that uses the process software application, the payment owed to the service provider is reconciled to the payment owed by the service provider to minimize the transfer of payments.

Figure 20:
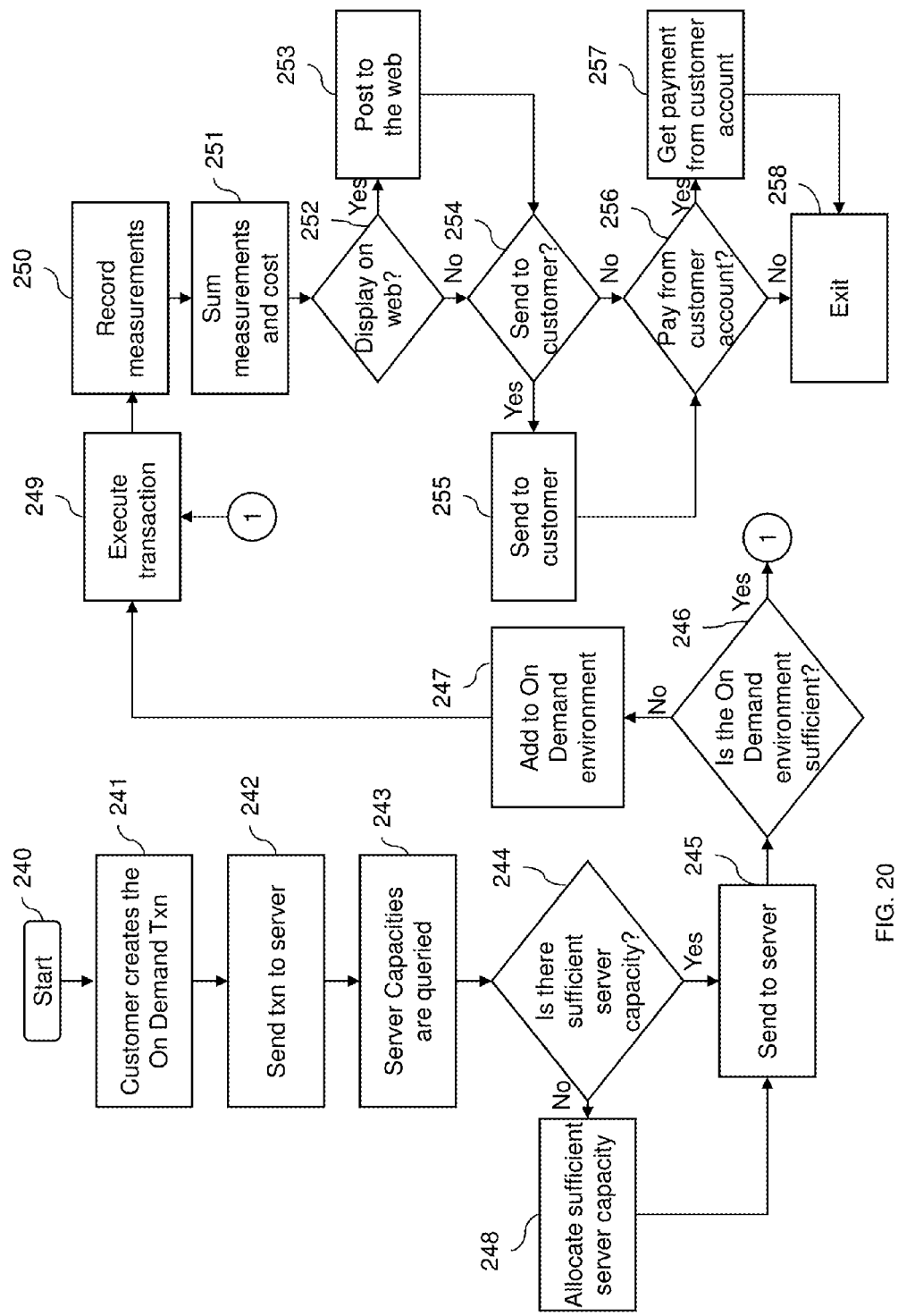
FIG. 20 is a schematic diagram of an on demand system according to embodiments herein.

In FIG. 20, Step 240 begins the On Demand process. A transaction is created than contains the unique customer identification, the requested service type and any service parameters that further specify the type of service 241. The transaction is then sent to the main server 242. In an On Demand environment the main server can initially be the only server, then as capacity is consumed other servers are added to the On Demand environment.

The server central processing unit (CPU) capacities in the On Demand environment are queried 243. The CPU requirement of the transaction is estimated, then the servers available CPU capacity in the On Demand environment are compared to the transaction CPU requirement to see if there is sufficient CPU available capacity in any server to process the transaction 244. If there is not sufficient server CPU available capacity, then additional server CPU capacity is allocated to process the transaction 248. If there was already sufficient Available CPU capacity then the transaction is sent to a selected server 245.

Before executing the transaction, a check is made of the remaining On Demand environment to determine if the environment has sufficient available capacity for processing the transaction. This environment capacity consists of such things as but not limited to network bandwidth, processor memory, storage etc. 246. If there is not sufficient available capacity, then capacity will be added to the On Demand environment 247. Next the required software to process the transaction is accessed, loaded into memory, then the transaction is executed 249.

The usage measurements are recorded 250. The usage measurements consist of the portions of those functions in the On Demand environment that are used to process the transaction. The usage of such functions as, but not limited to, network bandwidth, processor memory, storage and CPU cycles are what is recorded. The usage measurements are summed, multiplied by unit costs and then recorded as a charge to the requesting customer 251. If the customer has requested that the On Demand costs be posted to a web site 252 then they are posted 253.

If the customer has requested that the On Demand costs be sent via e-mail to a customer address 254 then they are sent 255. If the customer has requested that the On Demand costs be paid directly from a customer account 256 then payment is received directly from the customer account 257. The last step is to exit the On Demand process 258.

The process software may be deployed, accessed and executed through the use of a virtual private network (VPN), which is any combination of technologies that can be used to secure a connection through an otherwise unsecured or untrusted network. The use of VPNs is to improve security and for reduced operational costs. The VPN makes use of a public network, usually the Internet, to connect remote sites or users together. Instead of using a dedicated, real-world connection such as leased line, the VPN uses "virtual" connections routed through the Internet from the company's private network to the remote site or employee.

The process software may be deployed, accessed and executed through either a remote-access or a site-to-site VPN. When using the remote-access VPNs the process software is deployed, accessed and executed via the secure, encrypted connections between a company's private network and remote users through a third-party service provider. The enterprise service provider (ESP) sets a network access server (NAS) and provides the remote users with desktop client software for their computers. The telecommuters can then dial a toll-free number or attach directly via a cable or DSL modem to reach the NAS and use their VPN client software to access the corporate network and to access, download and execute the process software.

When using the site-to-site VPN, the process software is deployed, accessed and executed through the use of dedicated equipment and large-scale encryption that are used to connect a companies multiple fixed sites over a public network such as the Internet.

The process software is transported over the VPN via tunneling which is the process of placing an entire packet within another packet and sending it over a network. The protocol of the outer packet is understood by the network and both points, called tunnel interfaces, where the packet enters and exits the network.

Figure 21:
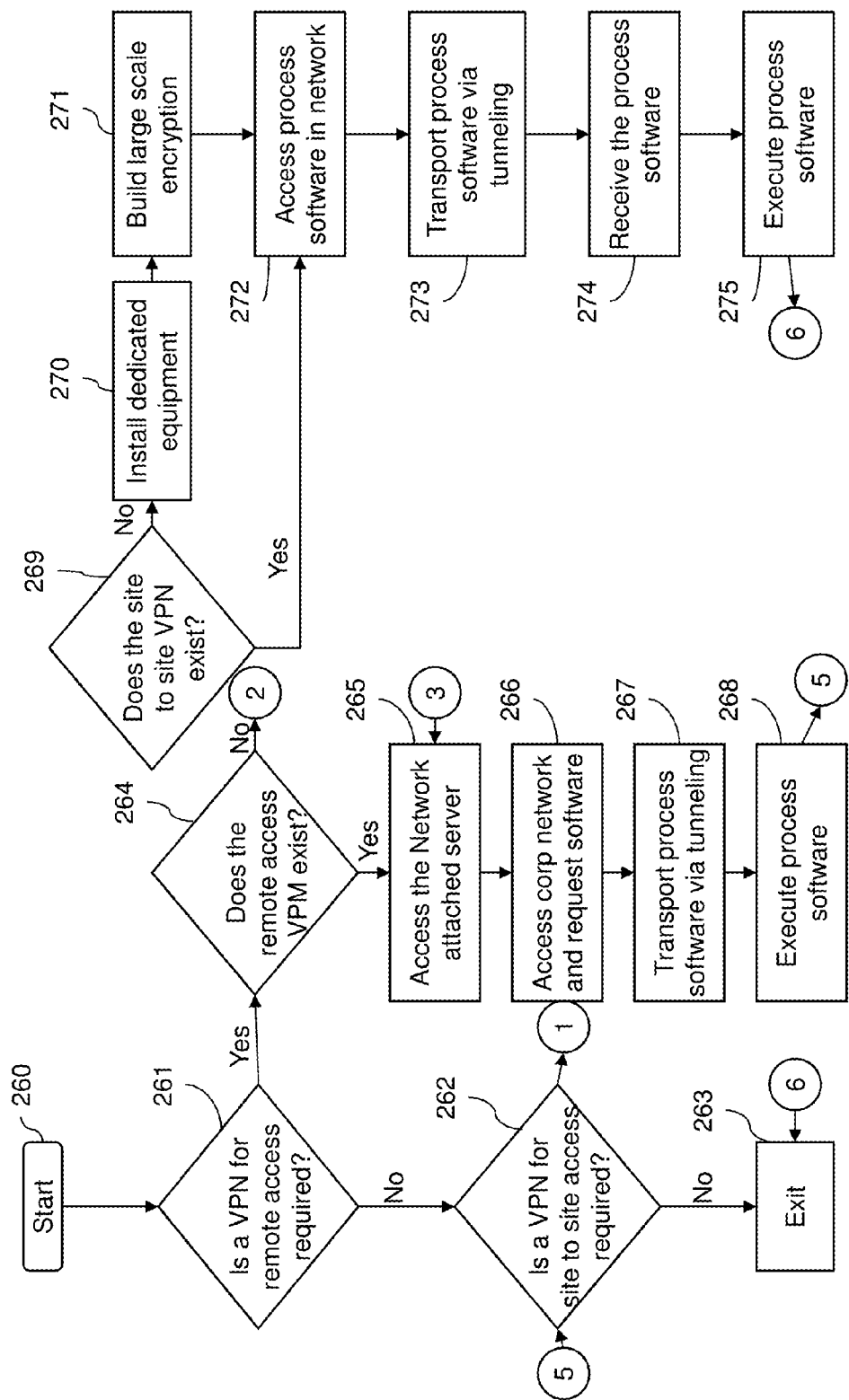
FIG. 21 is a schematic diagram of a virtual private network system according to embodiments herein.
Figure 22:
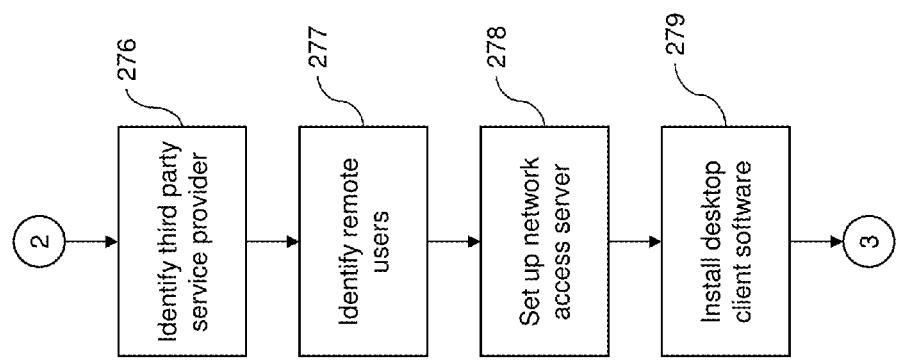
FIG. 22 is a schematic diagram of a virtual private network system according to embodiments herein.

In FIGS. 21 and 22, Step 260 begins the Virtual Private Network (VPN) process. A determination is made to see if a VPN for remote access is required 261. If it is not required, then proceed to 262. If it is required, then determine if the remote access VPN exists 264.

If it does exist, then proceed to 265. Otherwise identify the third party provider that will provide the secure, encrypted connections between the company's private network and the company's remote users 276. The company's remote users are identified 277. The third party provider then sets up a network access server (NAS) 278 that allows the remote users to dial a toll free number or attach directly via a cable or DSL modem to access, download and install the desktop client software for the remote-access VPN 279.

After the remote access VPN has been built or if it been previously installed, the remote users can then access the process software by dialing into the NAS or attaching directly via a cable or DSL modem into the NAS 265. This allows entry into the corporate network where the process software is accessed 266. The process software is transported to the remote user's desktop over the network via tunneling. That is the process software is divided into packets and each packet including the data and protocol is placed within another packet 267. When the process software arrives at the remote user's desktop, it is removed from the packets, reconstituted and then is executed on the remote users desktop 268.

A determination is made to see if a VPN for site to site access is required 262. If it is not required, then proceed to exit the process 263. Otherwise, determine if the site to site VPN exists 269. If it does exist, then proceed to 272. Otherwise, install the dedicated equipment required to establish a site to site VPN 270. Then build the large scale encryption into the VPN 271.

After the site to site VPN has been built or if it had been previously established, the users access the process software via the VPN 272. The process software is transported to the site users over the network via tunneling 273. That is the process software is divided into packets and each packet including the data and protocol is placed within another packet 274. When the process software arrives at the remote user's desktop, it is removed from the packets, reconstituted and is executed on the site users desktop 275. Proceed to exit the process 263.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments of the present systems and methods herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   displaying, on a user interface, at least one subject;
   displaying, on said user interface, a location for at least one user to enter at least one problem related to said subject;
   in response to entry of said at least one problem through said user interface, automatically acquiring factors related to said at least one problem from a record associated with said subject, said factors being categorized into dimensions of evidence, said record being stored on at least one computerized storage medium, and said automatically acquiring being performed using at least one computerized device operatively connected to said user interface and said at least one computerized storage medium;
   automatically generating questions related to said at least one problem and said factors using said at least one computerized device;
   in response to said questions, automatically generating answers to said questions by referring to sources, said sources being accessible by said at least one computerized device—and said generating of said answers being performed using said at least one computerized device;
   for each dimension of evidence, automatically calculating confidence measures of each of said answers using said at least one computerized device;
   combining said confidence measures of each of said answers for each dimension of evidence in order to calculate final confidence measures of each of said answers, said combining being performed using said at least one computerized device;
   generating a comparative evidence profile using said at least one computerized device and displaying said answers and said final confidence measures for each of said answers on said user interface with said comparative evidence profile, said comparative evidence profile comprising a chart that provides visual indications on said user interface of relative contributions of each of said dimensions of evidence to each of said final confidence measures of each of said answers and that comprises selectable features;
   displaying, on said user interface with said answers, said final confidence measures and said comparative evidence profile, details of said sources and said factors used to generate said answers on said user interface; and,
   upon receiving a selection of one of said selectable features of said chart through said user interface, automatically filtering said details of said sources and said factors so as to limit display of said details, said automatically filtering being performed by said at least one computerized device.

2. The method according to claim 1, further comprising maintaining a history of said questions, said answers, and said final confidence measures of each of said answers.

3. The method according to claim 1, said sources comprising first sources stored on said at least one computerized storage medium and second sources accessible online and said details of said sources comprising annotations to said sources.

4. The method according to claim 1, further comprising displaying how said sources contributed to said confidence measures of said answers on said user interface.

5. The method according to claim 1, said at least one problem comprising at least one question.

6. The method according to claim 1,
   said chart comprising a bar chart comprising groups of bars,
   each group of bars being associated with a specific dimension of evidence and being selectable to filter said details of said sources and said factors so as to limit displayed details of said sources and said factors to only those associated with said specific dimension of evidence, and,
   each bar within said group being associated with a specific answer and being selectable to further filter said details of said source and said factors so as to further limit said displayed details of said sources and said factors to only those associated with both said specific answer and said specific dimension of evidence.

7. A method comprising:
   displaying, on a user interface, at least one subject;
   displaying, on said user interface, a location for at least one user to enter at least one problem related to said at least one subject, said at least one problem comprising a medical problem;
   in response to entry of said at least one problem through said user interface, automatically acquiring factors related to said at least one problem from a medical record associated with said subject, said factors being categorized into dimensions of evidence, said dimensions of evidence comprising symptoms, family history and demographics, said record being stored on at least one computerized storage medium, and said automatically acquiring being performed using at least one computerized device operatively connected to said user interface and said at least one computerized storage medium;

automatically generating questions related to said at least one problem and said factors using said at least one computerized device;

receiving an indication of ones of said factors that should be ignored and ones of said factors that should be considered from said at least one user through said user interface;

in response to said questions, automatically generating answers to said questions by referring to said factors that should be considered and to sources, said sources being accessible by said at least one computerized device and said generating of said answers being performed using said at least one computerized device;

for each dimension of evidence, automatically calculating confidence measures of each of said answers using said at least one computerized device;

combining said confidence measures of each of said answers for each dimension of evidence in order to calculate final confidence measures of each of said answers, said combining being performed using said at least one computerized device;

generating a comparative evidence profile using said at least one computerized device and displaying said answers and said final confidence measures for each of said answers on said user interface with said comparative evidence profile, said comparative evidence profile comprising a chart that provides visual indications on said user interface of relative contributions of each of said dimensions of evidence to each of said final confidence measures of each of said answers and that comprises selectable features;

displaying, on said user interface with said answers, said final confidence measures and said comparative evidence profile, details of said sources and said factors used to generate said said answers; and, upon receiving a selection of one of said selectable features of said chart through said user interface, automatically filtering said details of said sources and said factors so as to limit display of said details, said automatically filtering being performed by said at least one computerized device.

8. The method according to claim 7, further comprising maintaining a history of said questions, said answers, and said final confidence measures of each of said answers.

9. The method according to claim 7, said sources comprising first sources stored on said at least one computerized storage medium and second sources accessible online and said details of said sources comprising annotations to said sources.

10. The method according to claim 7, further comprising displaying how said sources contributed to said confidence measures of said answers on said user interface.

11. The method according to claim 7, said at least one problem comprising at least one question.

12. The method according to claim 7,
said chart comprising a bar chart comprising groups of bars,
each group of bars being associated with a specific dimension of evidence and being selectable to filter said details of said sources and said factors so as to limit displayed details of said sources and said factors to only those associated with said specific dimension of evidence, and,
each bar within said group being associated with a specific answer and being selectable to further filter said details of said source and said factors so as to further limit said displayed details of said sources and said factors to only those associated with both said specific answer and said specific dimension of evidence.

13. A method comprising:
displaying, on a user interface, at least one subject;
displaying, on said user interface, a location for at least one user to enter at least one problem related to said subject, said at least one problem comprising a medical problem;
in response to entry of said at least one problem through said user interface, automatically acquiring factors related to said at least one problem from a medical record associated with said subject, said factors being categorized into dimensions of evidence, said dimensions of evidence comprising symptoms, family history and demographics, said record being stored on at least one computerized storage medium, and said automatically acquiring being performed using at least one computerized device operatively connected to said user interface and said at least one computerized storage medium;

displaying said factors categorized into said dimensions of evidence on said user interface;

receiving an indication of ones of said factors that should be ignored and ones of said factors that should be considered from said at least one user through said user interface;

automatically generating questions related to said at least one problem and said factors using said at least one computerized device;

in response to said questions, automatically generating answers to said questions by referring to said factors that should be considered and to sources, said sources being accessible by said at least one computerized device and said generating being performed using said at least one computerized device;

for each dimension of evidence, automatically calculating confidence measures of each of said answers using said at least one computerized device;

combining said confidence measures of each of said answers for each dimension of evidence in order to calculate final confidence measures of each of said answers;

generating a comparative evidence profile using said at least one computerized device and displaying said answers and said final confidence measures for each of said answers on said user interface with said comparative evidence profile, said comparative evidence profile comprising a chart that provides visual indications on said user interface of relative contributions of each of said dimensions of evidence to each of said final confidence measures of each of said answers and that has selectable features;

displaying, on said user interface with said answers, said final confidence measures and said comparative evidence profile, details of said sources and said factors used to generate said answers;

upon receiving a selection of one of said selectable features of said chart through said user interface, automatically filtering said details of said sources and said factors so as to limit display of said details, said automatically filtering being performed using said at least one computerized device;

receiving at least one of updated factors and updated information from said sources using said at least one computerized device;

automatically generating at least one updated answer based on said updated factors and updated information from said sources using said at least one computerized device;

automatically comparing said answers to said at least one updated answer to produce an update severity score for each question using said at least one computerized device, said update severity score being a measure of how much a set of answers for said question changed; and displaying said update severity score for each question on said user interface.

14. The method according to claim 13, further comprising maintaining a history of said questions, said answers, and said final confidence measures.

15. The method according to claim 13, said sources comprising first sources stored on said at least one computerized storage medium and second sources accessible online and said details of said sources comprising annotations to said sources.

16. The method according to claim 13, further comprising displaying how said sources contributed to said confidence measures of said answers on said user interface.

17. The method according to claim 13, said at least one problem comprising at least one question.

18. The method according to claim 13, said chart comprising a bar chart comprising groups of bars, each group of bars being associated with a specific dimension of evidence and being selectable to filter said details of said sources and said factors so as to limit displayed details of said sources and said factors to only those associated with said specific dimension of evidence, and, each bar within said group being associated with a specific answer and being selectable to further filter said details of said source and said factors so as to further limit said displayed details of said sources and said factors to only those associated with both said specific answer and said specific dimension of evidence.

19. A non-transitory computer readable storage medium readable by at least one computerized device, said non-transitory computer readable storage medium storing instructions executable by said at least one computerized device to perform a method comprising:

displaying on a user interface at least one subject;

displaying on said user interface a location for at least one user to enter at least one problem related to said subject;

in response to entry of said at least one problem through said user interface, automatically acquiring factors related to said at least one problem from a record associated with said subject, said factors being categorized into dimensions of evidence;

automatically generating questions related to said at least one problem and said factors;

in response to said questions, automatically generating answers to said questions by referring to sources;

for each dimension of evidence, automatically calculating confidence measures of each of said answers;

combining said confidence measures of each of said answers for each dimension of evidence in order to calculate final confidence measures of each of said answers;

generating a comparative evidence profile and displaying said answers and said final confidence measures for each of said answers with said comparative evidence profile on said user interface, said comparative evidence profile comprising a chart that provides visual indications of relative contributions of each of said dimensions of evidence to each of said final confidence measures of each of said answers and that has selectable features;

displaying, on said user interface with said answers, said final confidence measures and said comparative evidence profile, details of said sources and said factors used to generate said;

and, upon receiving a selection of one of said selectable features of said chart through said user interface, automatically filtering said details of said sources and said factors so as to limit display of said details.

20. The non-transitory computer readable storage medium according to claim 19, said method further comprising maintaining a history of said questions, said answers, and said final confidence measures.

21. The non-transitory computer readable storage medium according to claim 19, said sources comprising first sources stored on said at least one computerized storage medium and second sources accessible online and said details of said sources comprising annotations to said sources.

22. The non-transitory computer readable storage medium according to claim 19, further comprising displaying how said sources contributed to said confidence measures of said answers.

23. The non-transitory computer readable storage medium according to claim 19, said at least one problem comprising at least one question.

24. The non-transitory computer readable storage medium according to claim 19, said chart comprising a bar chart comprising groups of bars, each group of bars being associated with a specific dimension of evidence and being selectable to filter said details of said sources and said factors so as to limit displayed details of said sources and said factors to only those associated with said specific dimension of evidence, and, each bar within said group being associated with a specific answer and being selectable to further filter said details of said source and said factors so as to further limit said displayed details of said sources and said factors to only those associated with both said specific answer and said specific dimension of evidence.

* * * * *